US012727851B2

(12) United States Patent
Jung et al.

(10) Patent No.: US 12,727,851 B2
(45) Date of Patent: Sep. 8, 2026

(54) METHOD FOR PROVIDING INFORMATION ON M-MODE ULTRASOUND IMAGE, AND DEVICE FOR PROVIDING INFORMATION ON M-MODE ULTRASOUND IMAGE BY USING SAME

(71) Applicant: ONTACT HEALTH CO., LTD., Seoul (KR)

(72) Inventors: Sung Hee Jung, Seoul (KR); Hack Joon Shim, Seoul (KR); Da Wun Jeong, Gunpo-si (KR); Annes Choi, Seoul (KR)

(73) Assignee: ONTACT HEALTH CO., LTD., Seoul (KR)

( * ) Notice: Subject to any disclaimer, the term of this patent is extended or adjusted under 35 U.S.C. 154(b) by 0 days.

(21) Appl. No.: 18/859,151

(22) PCT Filed: Mar. 21, 2023

(86) PCT No.: PCT/KR2023/003736
§ 371 (c)(1),
(2) Date: Oct. 22, 2024

(87) PCT Pub. No.: WO2023/204457
PCT Pub. Date: Oct. 26, 2023

(65) Prior Publication Data

US 2025/0295376 A1 Sep. 25, 2025

(30) Foreign Application Priority Data

Apr. 22, 2022 (KR) ........................ 10-2022-0050236
Jan. 17, 2023 (KR) ........................ 10-2023-0006913

(51) Int. Cl.
*A61B 8/08* (2006.01)
*A61B 8/00* (2006.01)
(Continued)

(52) U.S. Cl.
CPC ............ *A61B 8/0883* (2013.01); *A61B 8/486* (2013.01); *A61B 8/5223* (2013.01);
(Continued)

(58) Field of Classification Search
CPC ..... A61B 8/0883; A61B 8/486; A61B 8/5223; G06N 3/08; G06T 2207/10132;
(Continued)

(56) References Cited

U.S. PATENT DOCUMENTS

2019/0388064 A1 12/2019 Kezurer et al.
2020/0178940 A1 6/2020 Hare, II et al.
2021/0259664 A1* 8/2021 Hare, II ................. A61B 8/469

FOREIGN PATENT DOCUMENTS

JP 2014-046122 A 3/2014
JP 5773281 B2 9/2015
(Continued)

OTHER PUBLICATIONS

Korean Notice of Allowance dated Nov. 6, 2024 issued on Application No. 10-2022-0050236.

*Primary Examiner* — Michael J Carey
*Assistant Examiner* — Maria Christina Talty
(74) *Attorney, Agent, or Firm* — INVENSTONE PATENT, LLC

(57) ABSTRACT

The present invention provides a method for providing information on an M-mode ultrasound image implemented by a processor and device using same, the method comprising the steps of: receiving an M-mode ultrasound image of a subject; segmenting a plurality of cardiac tomographic regions within the M-mode ultrasound image by using a segmentation model that is trained so as to segment the M-mode ultrasound image into a plurality of cardiac tomographic regions; and determining measurements for the plurality of segmented cardiac tomographic regions.

12 Claims, 32 Drawing Sheets

(51) Int. Cl.
*G06T 7/00* (2017.01)
*G06T 7/11* (2017.01)
*G16H 30/40* (2018.01)

(52) U.S. Cl.
CPC .............. *G06T 7/0012* (2013.01); *G06T 7/11* (2017.01); *G16H 30/40* (2018.01); *G06T 2207/10132* (2013.01); *G06T 2207/30048* (2013.01)

(58) Field of Classification Search
CPC . G06T 2207/20081; G06T 2207/20084; G06T 2207/30048; G06T 7/0012; G06T 7/11; G16H 30/40
See application file for complete search history.

(56) References Cited

FOREIGN PATENT DOCUMENTS

| | | | |
|---|---|---|---|
| JP | 2018-509229 | A | 4/2018 |
| JP | 2021-524767 | A | 9/2021 |
| KR | 10-2011-0128197 | A | 11/2011 |
| KR | 10-2014-0048740 | A | 4/2014 |
| KR | 10-2014-0092099 | A | 7/2014 |
| KR | 10-1423924 | B1 | 7/2014 |
| KR | 10-1625256 | B1 | 5/2016 |
| KR | 10-2019-0053807 | A | 5/2019 |
| KR | 10-2021-0115012 | A | 9/2021 |
| KR | 10-2022-0039881 | A | 3/2022 |
| KR | 10-2472886 | B1 | 12/2022 |
| KR | 10-20230061670 | A | 5/2023 |
| WO | 2020/044769 | A1 | 3/2020 |
| WO | 2021176237 | A1 | 9/2021 |

* cited by examiner

| | Pearson correlation coefficient (r) |
|---|---|
| LA diameter (unit: mm) | 0.91 |
| Aorta diameter (unit: mm) | 0.97 |

| | Pearson correlation coefficient (r) |
|---|---|
| Interventricular septum diameter at diastole (unit: mm) | 0.93 |
| LV internal diameter at diastole (unit: mm) | 0.95 |
| LV posterior wall diameter at diastole (unit: mm) | 0.81 |
| Interventricular septum diameter at systole (unit: mm) | 0.80 |
| LV internal diameter at systole (unit: mm) | 0.97 |
| LV posterior wall diameter at systole (unit: mm) | 0.85 |

METHOD FOR PROVIDING INFORMATION ON M-MODE ULTRASOUND IMAGE, AND DEVICE FOR PROVIDING INFORMATION ON M-MODE ULTRASOUND IMAGE BY USING SAME

CROSS-REFERENCE TO RELATED APPLICATIONS

This application is a National Stage filing under 35 U.S.C. 371 of International Application No. PCT/KR2023/003736, filed on Mar. 21, 2023, which claims the benefit of earlier filing date and right of priority to Korean Application No. 10-2022-0050236, filed on Apr. 22, 2022, and Korean Application No. 10-2023-0006913, filed on Jan. 17, 2023 in the Korean Intellectual Property Office, the contents of which are all hereby incorporated by reference herein in their entirety.

TECHNICAL FIELD

The present invention relates to a method for providing information on an M-mode ultrasound image, a device for providing information on an M-mode ultrasound image using the same, a method for providing information on an M-mode ultrasound image, and a device using the same.

BACKGROUND ART

A cardiac ultrasound examination is performed by projecting ultrasound waves on a three-dimensional structure of the heart in multiple planes to obtain cardiac images and measure hemodynamic variables.

At this time, a medical staff positions a ultrasound probe in a location where it is easy to obtain ultrasound images, so as to obtain multi-faceted images through anatomical structures around the heart, such as an intercostal space, and the like, and records the images by finding an appropriate tomographic region through rotation and tilting.

Among these, M-mode ultrasound images are ultrasound images that set a line of interest in a part of a subject to be observed and display the internal structure, and the like of the tissue included in the corresponding line over time.

M-mode ultrasound images of the heart may be primarily used to measure the thickness and the like of tissues, including the left ventricle or right ventricle of the heart. At this time, it may be common to measure the left ventricle internal dimension diastole (LVIDd) and the left ventricle internal dimension systole (LVIDs) of the heart at the end-diastole and end-systole of the heart, respectively. This is because the sealing volume of the left ventricle is largest at end-diastole and smallest at end-systole.

Meanwhile, M-mode ultrasound images of a subject that move periodically, such as the heart, have periodicity and may be used to derive clinically significant micro-measurements, such as tissue thickness, blood vessel diameter, and the like.

However, since the measurements may vary greatly depending on the skill level of the medical staff, there is a continuous demand for the development of a new information provision system capable of deriving highly accurate measurements from the M-mode images.

The background art of the invention has been prepared to more facilitate understanding of the present invention. It should not be understood that the matters described in the background art of the invention exist as prior arts.

SUMMARY OF THE DISCLOSURE

Meanwhile, in order to solve the above-mentioned problem, the present inventors attempted to develop an information providing system based on an artificial neural network trained to segment an M-mode ultrasound image into cardiac tomographic regions.

In particular, the present inventors were able to recognize that high-precision discrimination is possible for tomographic regions (e.g., the right ventricle anterior wall, the posterior wall of the left atrium, etc.) that are difficult to distinguish with the naked eye regardless of a type of M-mode (e.g., LA-Ao, or LV) by applying an artificial neural network.

As a result, the present inventors developed an information provision system based on an artificial neural network.

Meanwhile, the present inventors intended to design the information providing system to automatically determine measurements, such as an aorta diameter or a LA diameter, based on the regions segmented by the artificial neural network.

At this time, the present inventors attempted to design a method for determining measurements in different ways depending on the presence or absence of electrocardiogram (ECG) data that provides information in determining the measurements.

More specifically, the information providing system was constructed to automatically determine measurements by determining an end-diastole and an end-systole within segmented images when ECG data exists.

At this time, the information provision system was constructed to automatically determine measurements by utilizing the following three methods when ECG data does not exist.

1) Determine the periodicity.

2) Determine local maxima and local minima.

3) Calculate and determine a gradient.

Accordingly, the present inventors were able to expect that it would be possible to obtain M-mode-based measurements even in secondary and tertiary hospitals where it was difficult to obtain ECG data, by providing the information provision system.

Furthermore, the present inventors were able to expect that it would be possible to provide highly reliable analysis results for an M-mode ultrasound image regardless of the skill level of medical staff, by providing a new information provision system.

Accordingly, an object of the present invention is to provide a method for providing information on an M-mode ultrasound image, which is configured to classify a plurality of cardiac tomographic regions from a received M-mode ultrasound image using an artificial neural network-based segmentation model, and to determine measurements therefrom, and a device using the same.

The objects of the present invention are not limited to the aforementioned objects, and other objects, which are not mentioned above, will be apparent to those skilled in the art from the following description.

One aspect of the present invention provides a method for providing information on an M-mode ultrasound image. The method is a method for providing information on an M-mode ultrasound image implemented by a processor, including receiving an M-mode ultrasound image of a subject; segmenting a plurality of cardiac tomographic regions within the M-mode ultrasound image, respectively, by using a segmentation model that is trained so as to segment the M-mode ultrasound image into the plurality of cardiac tomographic regions by inputting the M-mode ultrasound image; and determining measurements for the plurality of segmented cardiac tomographic regions.

According to a feature of the present invention, the method may further include, after the segmenting step, receiving an electrocardiogram (ECG) for the subject; and determining end-diastole and end-systole based on the ECG. At this time, the determining of the measurements may include determining the measurements based on the end-diastole and the end-systole.

According to another feature of the present invention, the method may further include, after the segmenting step, determining periodicity for the plurality of cardiac tomographic regions. At this time, the determining of the measurements may include determining the measurements based on the periodicity.

According to yet another feature of the present invention, the determining of the periodicity may include calculating the degree of auto-correlation for the plurality of cardiac tomographic regions; determining peaks based on the degree of auto-correlation; and determining periodicity based on the peaks.

According to yet another feature of the present invention, the determining of the periodicity may include calculating the degree of cross-correlation for adjacent regions of the plurality of cardiac tomographic regions; determining peaks based on the degree of cross-correlation; and determining periodicity based on the peaks.

According to yet another feature of the present invention, the method may further include, after the segmenting step, determining a plurality of local maxima and a plurality of local minima for the plurality of cardiac tomographic regions. At this time, the determining of the measurements may include determining the measurements based on the local maxima and the local minima.

According to yet another feature of the present invention, the method may further include, after the segmenting step, calculating a gradient for the plurality of cardiac tomographic regions and determining the measurements based on the gradient.

According to yet another feature of the present invention, method may further include, after the segmenting step, selectively receiving the ECG for the subject.

According to yet another feature of the present invention, method may further include, when the ECG is received, after the receiving step, determining end-diastole and end-systole based on the ECG. Furthermore, the determining of the measurements may include determining the measurements based on the end-diastole and the end-systole.

According to yet another feature of the present invention, the method may further include, when the ECG is not received, after the receiving step, determining periodicity for the plurality of cardiac tomographic regions, in which the determining of the measurements may include determining the measurements based on the periodicity.

According to yet another feature of the present invention, the method may further include, when the ECG is not received, after the segmenting step, determining a plurality of local maxima and a plurality of local minima for the plurality of cardiac tomographic regions, in which the determining of the measurements may include determining the measurements based on the plurality of local maxima and the plurality of local minima.

According to yet another feature of the present invention, the method may further include, when the ECG is not received, after the segmenting step, calculating a gradient for the plurality of cardiac tomographic regions, in which the determining of the measurements may include determining the measurements based on the gradient.

According to yet another feature of the present invention, the method may further include, after the determining of the measurements, determining an entropy value; and verifying the measurements based on the entropy value.

According to yet another feature of the present invention, the plurality of cardiac tomographic regions may be at least two regions selected from the RV anterior wall, the right ventricle (RV), the anterior wall of aorta, the aorta, the posterior wall of aorta, the left atrium (LA), and the posterior wall of LA, and the measurements may be an aorta diameter or a LA diameter.

According to yet another feature of the present invention, the plurality of cardiac tomographic regions may be at least two regions selected from the RV anterior wall, the right ventricle, the interventricular septum (IVS), the left ventricle (LV), and the LV posterior wall, and the measurements may be at least one of an IVS diameter, an LV internal diameter (LVID), and an LV posterior wall diameter.

According to yet another feature of the present invention, the IVS diameter includes an IVS diameter at diastole and an IVS diameter at systole, the LVID includes an LVID at diastole and an LVID at systole, and the LV posterior wall diameter includes an LV posterior wall diameter at diastole and an LV posterior wall diameter at systole.

According to yet another feature of the present invention, the method may further include, after the segmenting step, removing the segmented regions other than the M-mode region or filling holes within the segmented regions so as to obtain a plurality of post-processed cardiac tomographic regions. At this time, the determining of the measurements may include determining the measurements based on the plurality of post-processed cardiac tomographic regions.

Another aspect of the present invention provides a device for providing information on an M-mode ultrasound image. The device includes a communication unit configured to receive an M-mode ultrasound image of a subject; and a processor functionally connected with the communication unit. At this time, the processor may be configured to segment a plurality of cardiac tomographic regions within the M-mode ultrasound image, respectively, by using a segmentation model that is trained so as to segment the M-mode ultrasound image into the plurality of cardiac tomographic regions by inputting the M-mode ultrasound image; and determine measurements for the plurality of segmented cardiac tomographic regions.

According to a feature of the present invention, the communication unit may be further configured to receive an electrocardiogram (ECG) for the subject. At this time, the processor may be further configured to determine end-diastole and end-systole based on the ECG, and determine the measurements based on the end-diastole and the end-systole.

According to another feature of the present invention, the processor may be further configured to determine periodicity for the plurality of cardiac tomographic regions, and determine the measurements based on the periodicity.

According to yet another feature of the present invention, the processor may be further configured to calculate the degree of auto-correlation for the plurality of cardiac tomographic regions, determine peaks based on the degree of auto-correlation, and determine periodicity based on the peaks.

According to yet another feature of the present invention, the processor may be further configured to calculate the degree of cross-correlation for adjacent regions of the plurality of cardiac tomographic regions, determine peaks based on the degree of cross-correlation, and determine periodicity based on the peaks.

According to yet another feature of the present invention, the processor may be further configured to determine a plurality of local maxima and a plurality of local minima for the plurality of cardiac tomographic regions and determine the measurements based on the plurality of local maxima and the plurality of local minima.

According to yet another feature of the present invention, the processor may be further configured to calculate a gradient for the plurality of cardiac tomographic regions, and determine the measurements based on the gradient.

According to yet another feature of the present invention, the communication unit may be further configured to selectively receive an ECG for the subject.

According to yet another feature of the present invention, the processor may be further configured to determine end-diastole and end-systole based on the ECG, and determine the measurements based on the end-diastole and the end-systole, when the ECG is received.

According to yet another feature of the present invention, the processor may be further configured to determine periodicity for the plurality of cardiac tomographic regions, and determine the measurements based on the periodicity, when the ECG is not received.

According to yet another feature of the present invention, the processor may be further configured to determine a plurality of local maxima and a plurality of local minima for the plurality of cardiac tomographic regions and determine the measurements based on the plurality of local maxima and the plurality of local minima, when the ECG is not received.

According to yet another feature of the present invention, the processor may be further configured to calculate a gradient for the plurality of cardiac tomographic regions, and determine the measurements based on the gradient, when the ECG is not received.

According to yet another feature of the present invention, the processor may be further configured to determine an entropy value and verify the measurements based on the entropy value.

According to yet another feature of the present invention, the processor may be further configured to remove the segmented regions other than the M-mode region or fill holes within the segmented regions so as to obtain a plurality of post-processed cardiac tomographic regions, and determine the measurements based on the plurality of post-processed cardiac tomographic regions.

Details of other embodiments will be included in the detailed description of the invention and the accompanying drawings.

According to the present invention, it is possible to provide highly reliable cardiac ultrasound diagnosis results by providing a system for providing information on an M-mode ultrasound image based on an artificial neural network configured to segment cardiac tomographic regions using an M-mode ultrasound image.

In particular, it is possible to faster and more accurately provide cardiac ultrasound diagnostic results, by providing an information provision system configured to automatically measure measurements based on segmented cardiac tomography regions.

That is, it is possible to provide highly reliable analysis results for M-mode ultrasound images regardless of the skill level of medical staff, and to contribute to establishing more accurate decision-making and treatment plans at an image analysis step.

Furthermore, it is possible to obtain M-mode-based measurements even in secondary and tertiary hospitals where it is difficult to obtain ECG data, by providing an information provision system with different methods for determining measurements depending on presence or absence of ECG.

The effects according to the present invention are not limited to the contents exemplified above, and further various effects are included in the present specification.

BRIEF DESCRIPTION OF THE DRAWINGS

FIGS. 9A to 9F illustrate evaluation results for automatic measurement according to an information provision method according to various embodiments.

DETAILED DESCRIPTION OF THE DISCLOSURE

Figure 1:
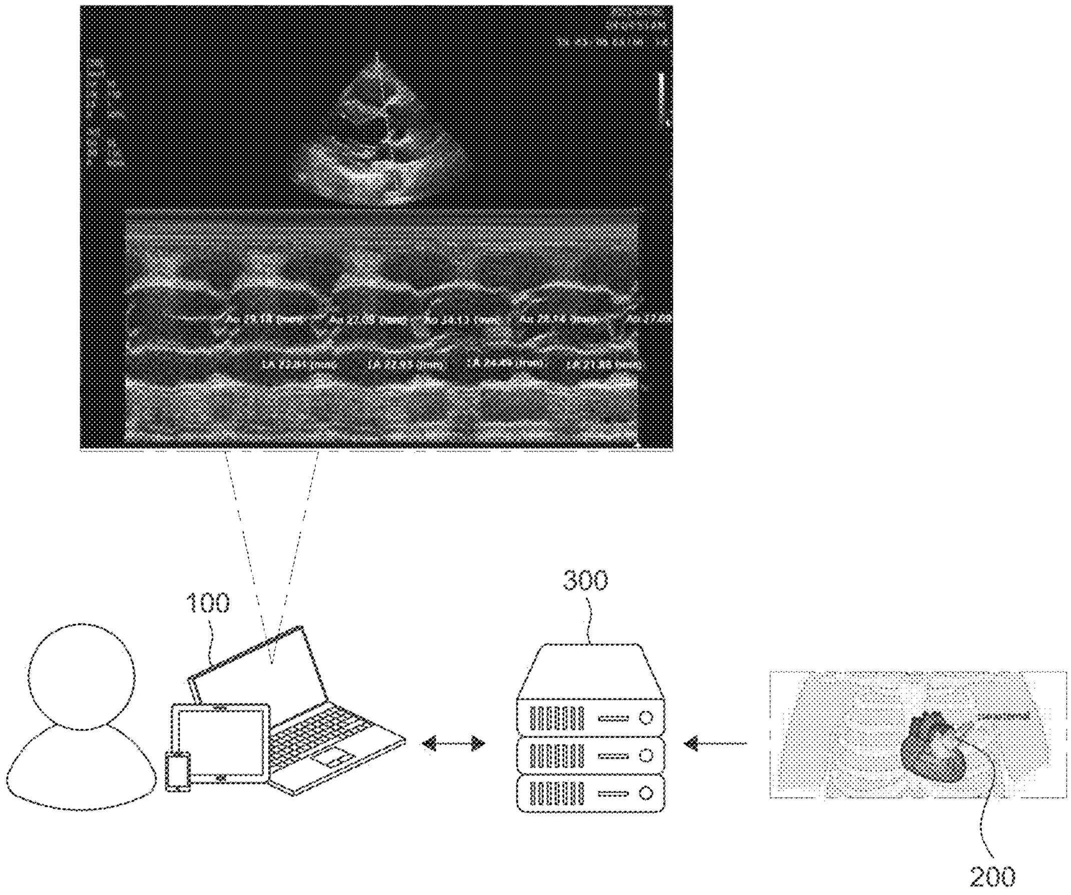
FIG. 1 illustrates a system for providing information on an M-mode ultrasound image using a device for providing information on an M-mode ultrasound image according to an embodiment of the present invention.

Advantages of the present invention, and methods for accomplishing the same will be more clearly understood from exemplary embodiments to be described in detail below with reference to the accompanying drawings. However, the present invention is not limited to the following exemplary embodiments but may be implemented in various different forms. The exemplary embodiments are provided only to make description of the present invention complete and to fully provide the scope of the present invention to a person having ordinary skill in the art to which the present invention pertains with the category of the invention.

The shapes, sizes, ratios, angles, numbers, and the like illustrated in the drawings for describing the exemplary embodiments of the present invention are merely examples, and the present invention is not limited thereto. Further, in describing the present invention, a detailed explanation of known related technologies will be omitted when it is determined to unnecessarily obscure the subject matter of the present invention. The terms such as "including," "having," and "consist of" used herein are generally intended to allow other components to be added unless the terms are used with the term "only". Any references to singular may include plural unless expressly stated otherwise.

Components are interpreted to include an ordinary error range even if not expressly stated.

The features of various exemplary embodiments of the present invention may be partially or entirely coupled or combined with each other and may be interlocked and operated in technically various ways to be sufficiently appreciated by those skilled in the art, and the exemplary embodiments may be implemented independently of or in association with each other.

For the clarity of the interpretation of the present invention, hereinafter, the terms used in the present invention will be defined.

The term "subject" as used herein may mean any subject to receive information on an M-mode ultrasound image. Meanwhile, the subject disclosed in the present invention may be all mammals other than humans, but is not limited thereto.

As used in the present disclosure, the term "M-mode ultrasound image" may mean an ultrasound image that sets a line of interest in a part of a subject to be observed and displays the internal structure of a tissue (particularly, a cardiac tomographic structure) included in the corresponding line over time.

Preferably, the M-mode ultrasound image may be an M-mode ultrasound image of the cardiac region of the subject, but is not limited thereto.

According to a feature of the present invention, the M-mode ultrasound image may be an M-mode image for left atrium-aorta (LA-Ao) analysis or left ventricle (LV) analysis.

As used in the present disclosure, the term "the plurality of cardiac tomographic regions" may mean a plurality of regions of the cardiac structure visible on the M-mode image.

According to a feature of the present invention, the plurality of cardiac tomographic regions may include at least two regions selected from the right ventricle anterior wall, the right ventricle (RV), the anterior wall of the aorta, the aorta, the posterior wall of aorta, the left atrium (LA), and the posterior wall of LA.

According to another feature of the present invention, the plurality of cardiac tomographic regions may be at least two regions selected from the RV anterior wall, the right ventricle, the interventricular septum (IVS), the left ventricle (LV), and the LV posterior wall.

As used in the present disclosure, the term "segmentation model" may be a model configured to output cardiac tomographic regions by inputting an M-mode ultrasound image.

More specifically, the segmentation model may be a model configured to segment a plurality of cardiac tomographic regions by inputting an M-mode ultrasound image (in particular, an M-mode region).

For example, the segmentation model may be a model configured to probabilistically segment and output each of the RV anterior wall, the right ventricle, the anterior wall of aorta, the aorta, the posterior wall of aorta, the left atrium, and the LA posterior wall, respectively, by inputting the M-mode ultrasound image.

In addition, the segmentation model may be a model configured to probabilistically segment and output the right ventricle, the interventricular septum, the left ventricle, and the LV posterior wall, respectively, by inputting the M-mode ultrasound image.

Meanwhile, the segmentation model may be on the basis of at least one algorithm selected from DenseNet-121, U-net, VGG net, DenseNet, and Fully Convolutional Network (FCN) with an encoder-decoder structure, SegNet, DeconvNet, deep neural network (DNN) such as DeepLAB V3+, SqueezeNet, Alexnet, ResNet18, MobileNet-v2, GoogLeNet, Resnet-v2, Resnet50, RetinaNet, Resnet101, and Inception-v3. Furthermore, the segmentation model may be an ensemble model based on at least two algorithm models among the aforementioned algorithms.

As used in the present disclosure, the term "measurements" may mean numerical values, such as thickness, diameter, and the like, that may be measured from the plurality of cardiac tomographic regions.

According to a feature of the present invention, the measurements may be an aorta diameter or an LA diameter.

According to another feature of the present invention, the measurements may be at least one of an IVS diameter, an LV internal diameter (LVID) and an LV posterior wall diameter.

Here, the IVS diameter may include an IVS diameter at diastole and an IVS diameter at systole, and the LVID may include an LVID at diastole and an LVID at systole. Furthermore, the LV posterior wall diameter includes a LV posterior wall diameter at diastole and a LV posterior wall diameter at systole.

According to yet another feature of the present invention, the measurements may be determined from the segmentation results of the plurality of cardiac tomographic regions for the M-mode ultrasound image and an electrocardiogram (ECG).

More specifically, the measurements may be determined based on the end-diastole and end-systole for the cardiac tomographic regions determined from the ECG.

According to yet another feature of the present invention, the measurements may be determined from only the segmentation results of the plurality of cardiac tomographic regions for the M-mode ultrasound image.

More specifically, the measurements may be determined based on periodicity of the segmented cardiac tomographic regions.

At this time, the periodicity may be determined based on the degree of auto-correlation for the plurality of cardiac tomographic regions and peaks based on the degree of auto-correlation.

However, it is not limited thereto, and the periodicity may also be determined based on the degree of cross-correlation for adjacent regions of the plurality of cardiac tomographic regions.

According to yet another feature of the present invention, the measurements may be determined based on a plurality of local maxima and a plurality of local minima of the segmented cardiac tomographic regions.

According to yet another feature of the present invention, the measurements may be determined based on gradient values of the segmented cardiac tomographic regions.

Hereinafter, a system for providing information on an M-mode ultrasound image using a device for providing information on an M-mode ultrasound image according to an embodiment of the present invention and a device for providing information on an M-mode ultrasound image will be described with reference to FIGS. 1 and 2A and 2B.

FIG. 1 illustrates a system for providing information on an M-mode ultrasound image using a device for providing information on an M-mode ultrasound image according to an embodiment of the present invention. FIG. 2A exemplarily illustrates a configuration of a medical staff device for receiving information on an M-mode ultrasound image according to an embodiment of the present invention. FIG. 2B exemplarily illustrates a configuration of a device for providing information on an M-mode ultrasound image according to an embodiment of the present invention.

First, an information provision system may be a system configured to provide information associated with an M-mode ultrasound image based on the M-mode ultrasound image of a subject. Referring to FIG. 1, the information provision system may be configured by a medical staff device 100 that receives information associated with an M-mode ultrasound image, an ultrasound image diagnosis device 200 that provides an M-mode ultrasound image, and an information provision server 300 that generates information on an M-mode ultrasound image based on the received M-mode ultrasound image.

First, next, the medical staff device 100 is an electronic device that provides a user interface for displaying information associated with an M-mode ultrasound image, and may include at least one of a smart phone, a tablet personal computer (PC), a laptop computer, and/or a PC.

The medical staff device 100 may receive prediction results associated with the M-mode ultrasound image of the subject from the information provision server 300 and display the received results on a display unit to be described below.

The information provision server 300 may include a general-purpose computer, a laptop computer, and/or a data server that performs various operations to determine information associated with the M-mode ultrasound image based on the M-mode ultrasound image provided from the ultrasound image diagnosis device 200, such as an ultrasound diagnosis device, and further, an ECG provided from an ECG measuring device (not illustrated). At this time, the information provision server 300 may be a device for accessing a web server for providing web pages or a mobile web server for providing mobile web sites, but is not limited thereto.

More specifically, the information provision server 300 receives an M-mode ultrasound image from the ultrasound image diagnosis device 200 and segments cardiac tomographic regions within the received M-mode ultrasound image. At this time, the information provision server 300 may segment cardiac tomographic regions from an M-mode ultrasound image using a prediction model.

Furthermore, the information provision server 300 may determine measurements such as a wall thickness, a tube diameter, etc. based on the segmented cardiac tomographic regions and/or the received ECG data.

The information provision server 300 may provide the determined measurements, further segmentation results, etc. to the medical staff device 100.

As such, the information provided from the information provision server 300 may be provided to a web page through a web browser installed on the medical staff device 100, or provided in the form of applications or programs. In various embodiments, such data may be provided in a form included in a platform in a client-server environment.

Next, components of the information provision server 300 of the present invention will be described in detail with reference to FIGS. 2A and 2B.

Figure 2A:
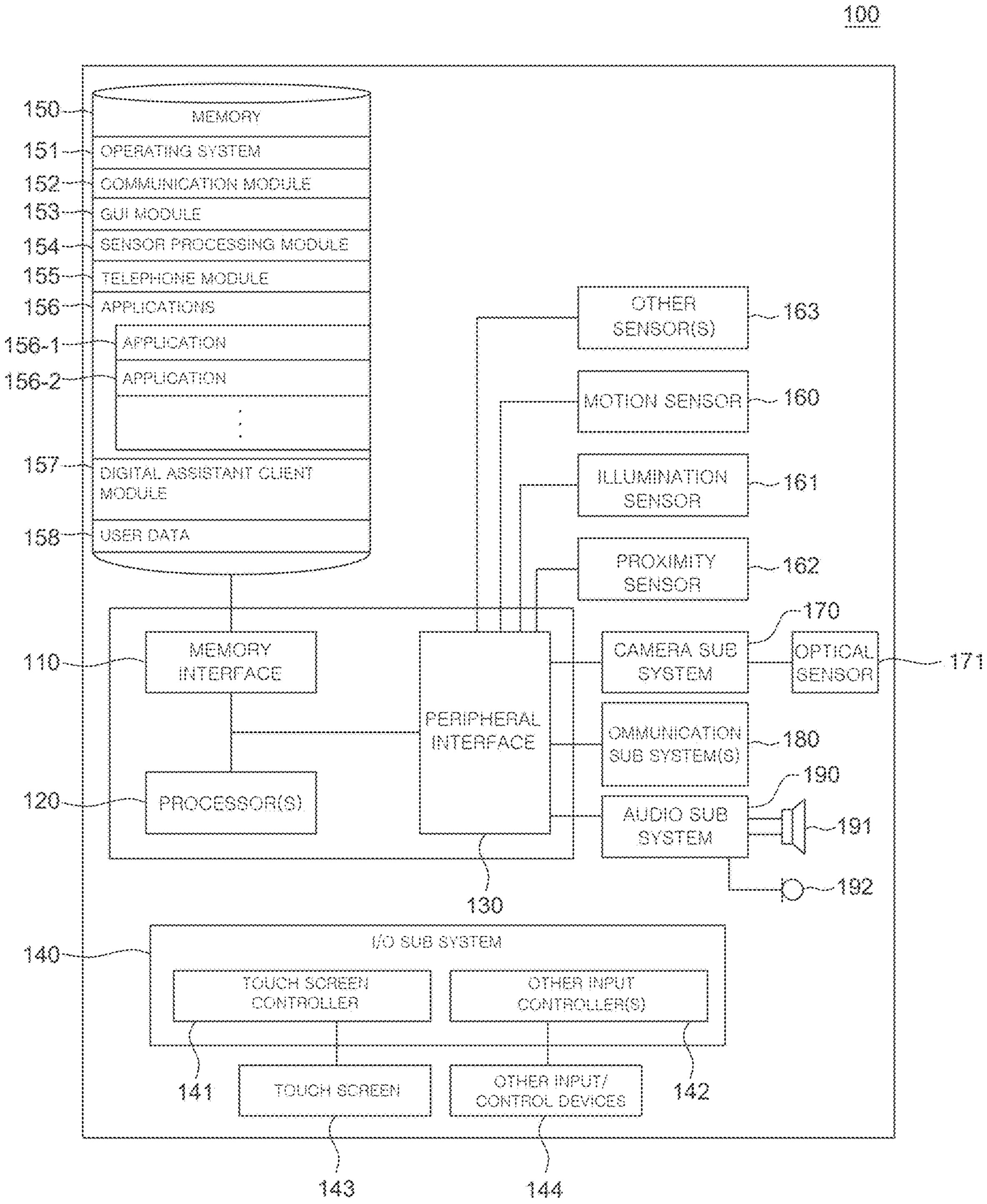
FIG. 2A is a block diagram illustrating a configuration of a medical staff device according to an embodiment of the present invention.

First, referring to FIG. 2A, the medical staff device 100 may include a memory interface 110, one or more processors 120, and a peripheral interface 130. Various components in the medical staff device 100 may be connected to each other by one or more communication buses or signal lines.

The memory interface 110 is connected to the memory 150 to transmit various data to the processors 120. Here, the memory 150 may include at least one type of storage medium of a flash memory type, a hard disk type, a multimedia card micro type, a card type memory (e.g., SD or XD memory, etc.), a RAM, an SRAM, a ROM, an EEPROM, a PROM, a network storage, a cloud, and a blockchain database.

In various exemplary embodiments, the memory 150 may store at least one or more of an operating system 151, a communication module 152, a graphical user interface (GUI) module 153, a sensor processing module 154, a phone module 155 and an application module 156. Specifically, the operating system 151 may include instructions for processing a basic system service and instructions for performing hardware operations. The communication module 152 may communicate with at least one of other one or more devices, computers and servers. The GUI module 153 may process a graphical user interface. The sensor processing module 154 may process sensor-related functions (e.g., processing a received voice input using one or more microphones 192). The phone module 155 may process phone-related functions. The application module 156 may perform various functions of the user application, such as electronic messaging, web browsing, media processing, searching, imaging, and other process functions. Further, the medical staff device 100 may store one or more software applications 156-1 and 156-2 (e.g., information provision applications) associated with any one type of service in the memory 150.

In various embodiments, the memory 150 may store a digital assistant client module 157 (hereinafter, referred to as a DA client module), and accordingly, may store instructions for performing client-side functions of a digital assistant and various user data 158.

On the other hand, the DA client module 157 may acquire a voice input, a text input, a touch input and/or a gesture input of the user through various user interfaces (e.g., an I/O subsystem 140) provided in the medical staff device 100.

In addition, the DA client module 157 may output audio-visual and tactile types of data. For example, the DA client module 157 may output data consisting of combinations of at least two or more of voice, sound, notifications, text messages, menus, graphics, video, animation, and vibration. In addition, the DA client module 157 may communicate with a digital assistant server (not illustrated) using a communication subsystem 180.

In various exemplary embodiments, the DA client module 157 may collect additional information on a surrounding environment of the medical staff device 100 from various sensors, subsystems and peripheral devices in order to configure a context associated with the user input. For example, the DA client module 157 may infer a user's intention by providing context information with the user input to the digital assistant server. Here, the context information that may be accompanied by the user input may include sensor information, for example, lighting, ambient noise, ambient temperature, images and videos in an ambient environment, and the like. For another example, the context information may include physical states of the medical staff device 100 (e.g., device orientation, device location, device temperature, power level, speed, acceleration, motion pattern, cellular signal strength, etc.). For yet another example, the context information may include information related to software states of the medical staff device 100 (e.g., processes running on the medical staff device 100, installed programs, previous and current network activities, background services, error logs, resource usage, etc.).

In various exemplary embodiments, the memory 150 may include added or deleted instructions, and furthermore, the medical staff device 100 may include additional configurations in addition to the configurations illustrated in FIG. 2A, or may also exclude some configurations.

The processor 120 may control the overall operation of the medical staff device 100 and execute various instructions to implement an interface that provides information associated with the M-mode ultrasound image by driving applications or programs stored in the memory 150.

The processor 120 may correspond to a computing device such as a central processing unit (CPU) or an application processor (AP). In addition, the processor 120 may be implemented in the form of an integrated chip (IC), such as a system on chip (SoC) integrated with various computing devices such as a neutral processing unit (NPU).

The peripheral interface 130 may be connected with various sensors, subsystems and peripheral devices to provide data so that the medical staff device 100 may perform various functions. Here, it may be understood that whether the medical staff device 100 performs any function is performed by the processor 120.

The peripheral interface 130 may receive data from a motion sensor 160, a lighting sensor (optical sensor) 161 and a proximity sensor 162, so that the medical staff device 100 may perform orientation, lighting, and proximity sensing functions, etc. For another example, the peripheral interface 130 may receive data from other sensors 163 (positioning system-GPS receiver, temperature sensor, and biometric sensor), so that the medical staff device 100 may perform functions associated with other sensors 163.

In various exemplary embodiments, the medical staff device 100 may include a camera subsystem 170 connected with the peripheral interface 130 and an optical sensor 171 connected thereto, so that the medical staff device 100 may perform various photographing functions such as photographing, video clip recording, etc.

In various exemplary embodiments, the medical staff device 100 may include a communication subsystem 180 connected with the peripheral interface 130. The communication subsystem 180 is configured as one or more wired/wireless networks, and may include various communication ports, radio frequency transceivers, and optical transceivers.

In various exemplary embodiments, the medical staff device 100 includes an audio subsystem 190 connected with the peripheral interface 130, and the audio subsystem 190 includes one or more speakers 191 and one or more microphones 192, so that the medical staff device 100 may perform a voice-operating function, such as voice recognition, voice reproduction, digital recording, and phone functions, etc.

In various exemplary embodiments, the medical staff device 100 may include an I/O subsystem 140 connected with the peripheral interface 130. For example, the I/O subsystem 140 may control a touch screen 143 included in the medical staff device 100 through a touch screen controller 141. As an example, the touch screen controller 141 may detect contact and motion of the user or interruption of the contact and motion by using any one of a plurality of touch sensing techniques, such as capacitive, resistive, infrared, and surface elastic wave techniques, proximity sensor arrays, etc. For another example, the I/O subsystem 140 may control other input/control devices 144 included in the medical staff device 100 through other input controller(s) 142. As an example, the other input controller(s) 142 may control a pointer device, such as one or more buttons, rocker switches, thumb-wheels, infrared ports, USB ports, and styluses.

Figure 2B:
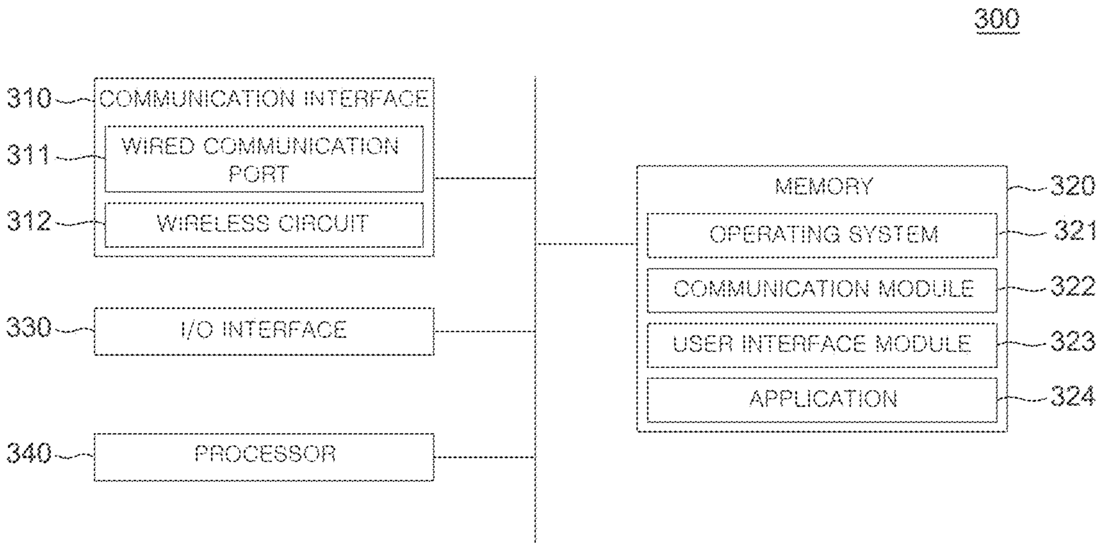
FIG. 2B is a block diagram illustrating a configuration of an information provision server according to an embodiment of the present invention.

Next, referring to FIG. 2B, the information provision server 300 may include a communication interface 310, a memory 320, an I/O interface 330, and a processor 340, which may communicate with each other through one or more communication buses or signal lines.

The communication interface 310 may be connected with the medical staff device 100, the ultrasound image diagnosis device 200, and the ECG measurement device (not illustrated) via a wired/wireless communication network to transmit and receive data. For example, the communication interface 310 may receive an M-mode ultrasound image from the ultrasound image diagnosis device 200 and an ECG from the ECG measurement device (not illustrated), and transmit information associated with measurements determined therefrom to the medical staff device 100.

Meanwhile, the communication interface 310 to transmit and receive such data includes a communication port 311 and a wireless circuit 312, in which the wired communication port 311 may include one or more wired interfaces, such as Ethernet, a universal serial bus (USB), a firewire, and the like. In addition, the wireless circuit 312 may transmit and receive data with an external device through an RF signal or an optical signal. In addition, the wireless communication may use at least one of a plurality of communication standards, protocols and technologies, such as GSM, EDGE, CDMA, TDMA, Bluetooth™ wireless communication protocol, Wi-Fi™ wireless local area network communication, VOIP, and Wi-MAX, or any other suitable communication protocols.

The memory 320 may store various data used in the information provision server 300. For example, the memory 320 may store an M-mode ultrasound image, or store a segmentation model trained to segment cardiac tomographic regions within the M-mode ultrasound image.

In various exemplary embodiments, the memory 320 may include a volatile or nonvolatile recording medium capable of storing various data, instructions, and information. For example, the memory 320 may include at least one type of storage medium of a flash memory type, a hard disk type, a multimedia card micro type, a card type memory (e.g., an SD or XD memory, etc.), a RAM, an SRAM, a ROM, an EEPROM, a PROM, a network storage, a cloud, and a blockchain database.

In various exemplary embodiments, the memory 320 may store at least one configuration of an operating system 321, a communication module 322, a user interface module 323, and one or more applications 324.

The operating system 321 (e.g., embedded operating system such as LINUX, UNIX, MAC™ operating system, Windows™ operating system, VxWorks, etc.) may include various software components and drivers for controlling and managing general system operations (e.g., memory management, storage device control, power management, etc.), and may support communication among various hardware, firmware, and software components.

The communication module 323 may support communication with other devices through the communication interface 310. The communication module 320 may include various software components for processing the data received by the wired communication port 311 or the wireless circuit 312 of the communication interface 310.

The user interface module 323 may receive a request or input of the user from a keyboard, a touch screen, a microphone, etc. through the I/O interface 330, and may provide a user interface on the display.

The application 324 may include a program or module that is configured to be executed by one or more processors 330. Here, the application for providing information associated with the M-mode ultrasound image may be implemented on a server farm.

The I/O interface 330 may connect at least one of I/O devices (not illustrated) of the information provision server 300, for example, at least one of a display, a keyboard, a touch screen and a microphone, with the user interface module 323. The I/O interface 330 may receive a user input (e.g., voice input, keyboard input, touch input, etc.) with the user interface module 323, and process instructions according to the received input.

The processor 340 is connected with the communication interface 310, the memory 320, and the I/O interface 330 to control the overall operation of the information provision server 300, and may perform various instructions for providing information through applications or programs stored in the memory 320.

The processor 340 may correspond to a computing device such as a central processing unit (CPU) or an application processor (AP). In addition, the processor 340 may be implemented in the form of an integrated chip (IC), such as a system on chip (SoC) integrated with various computing devices. Alternatively, the processor 340 may include a module for calculating an artificial neural network model, such as a neural processing unit (NPU).

In various embodiments, the processor 340 may be configured to segment and provide cardiac tomographic regions within the M-mode ultrasound image using prediction models. Optionally, the processor 340 may be configured to provide information on measurements obtainable from the M-mode ultrasound image.

Hereinafter, a method for providing information on an M-mode ultrasound image according to an embodiment of the present invention will be described in detail with reference to FIGS. 3 to 6.

Figure 3:
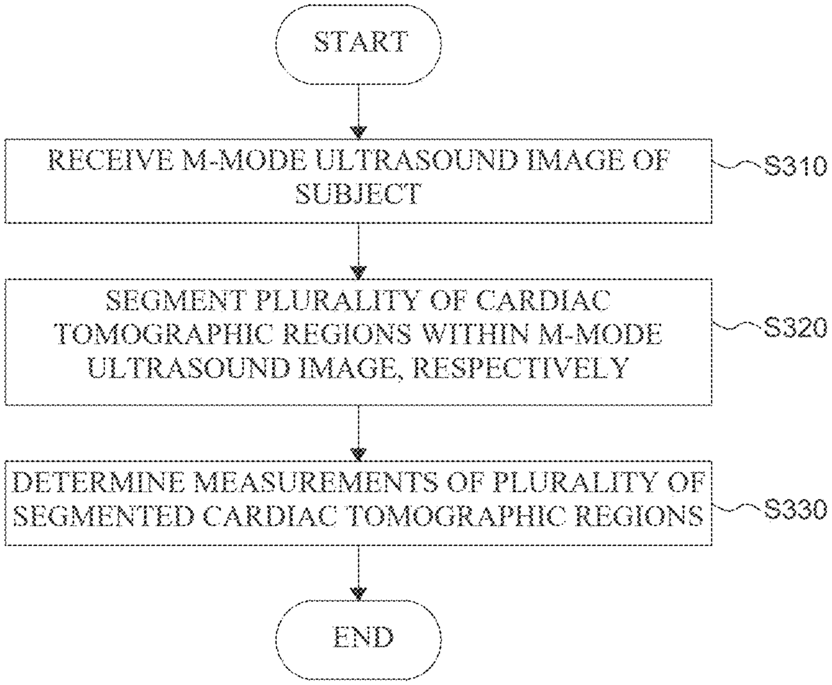
FIG. 3 illustrates a process of a method for providing information on an M-mode ultrasound image according to an embodiment of the present invention.
Figure 4:
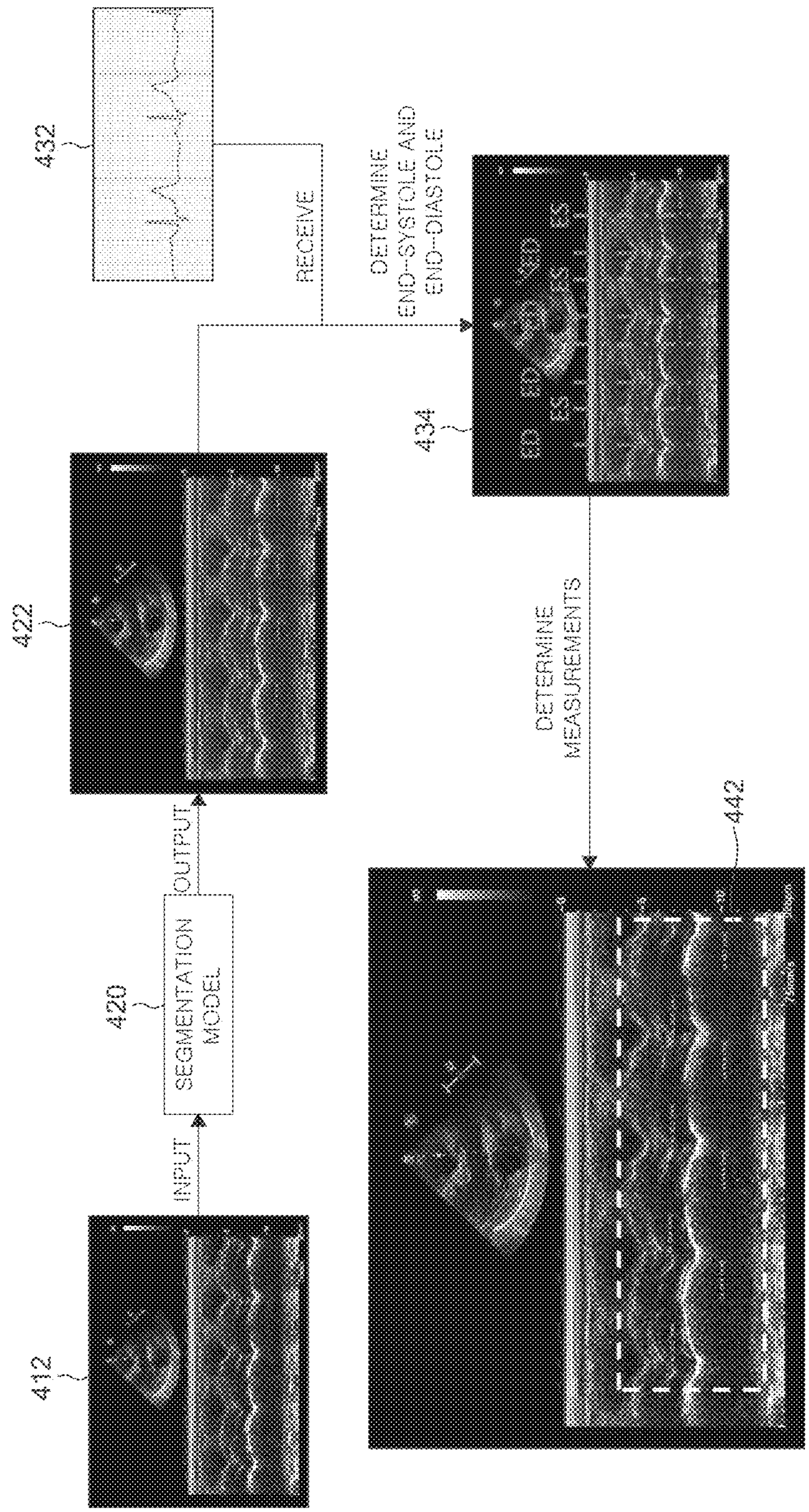
FIG. 4 exemplarily illustrates a process of a method for providing information on an M-mode ultrasound image according to an embodiment of the present invention.
Figure 5A:
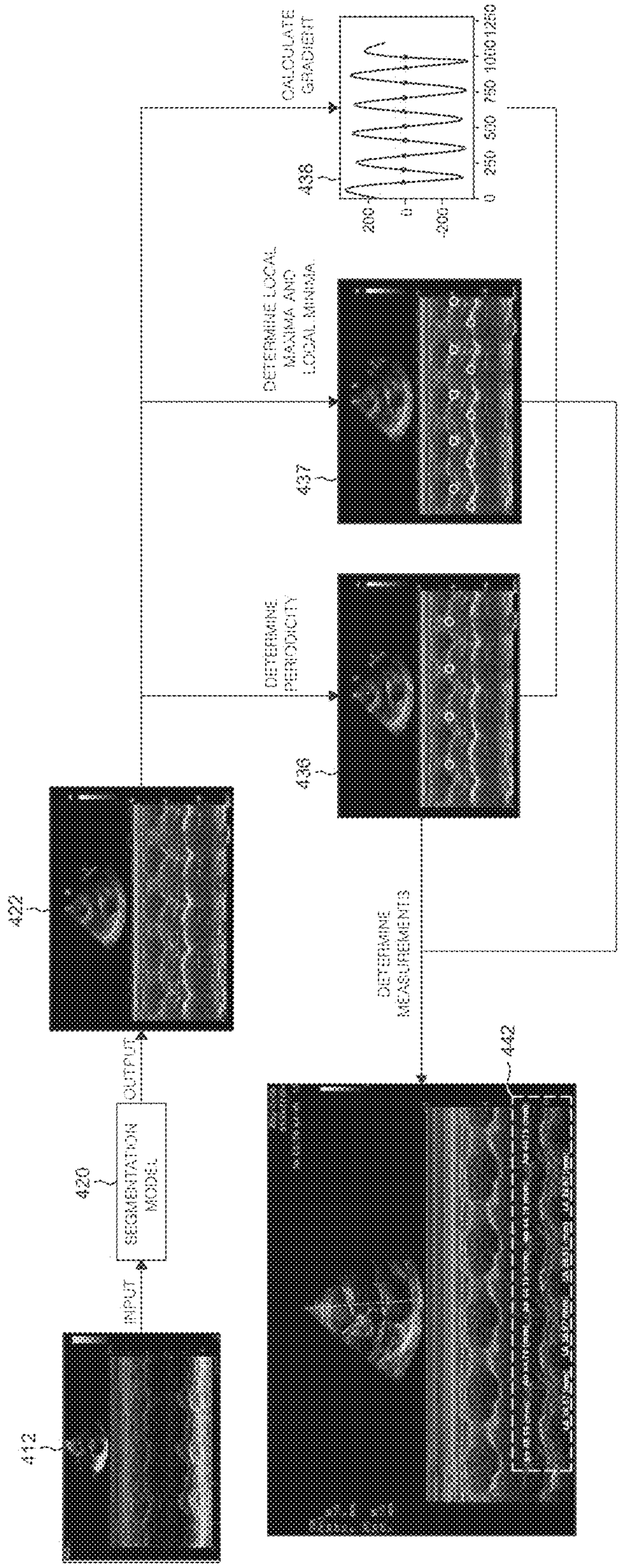
FIGS. 5A and 5B exemplarily illustrate a process of a method for providing information on an M-mode ultrasound image according to another embodiment of the present invention.
Figure 5B:
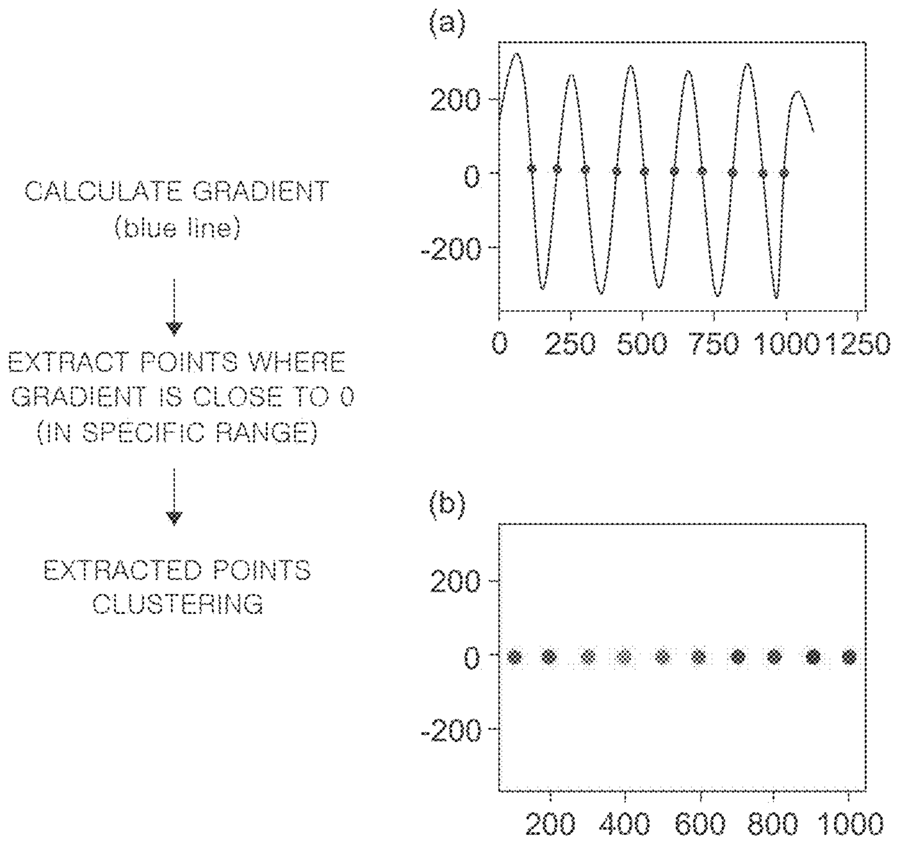
Figure 6:
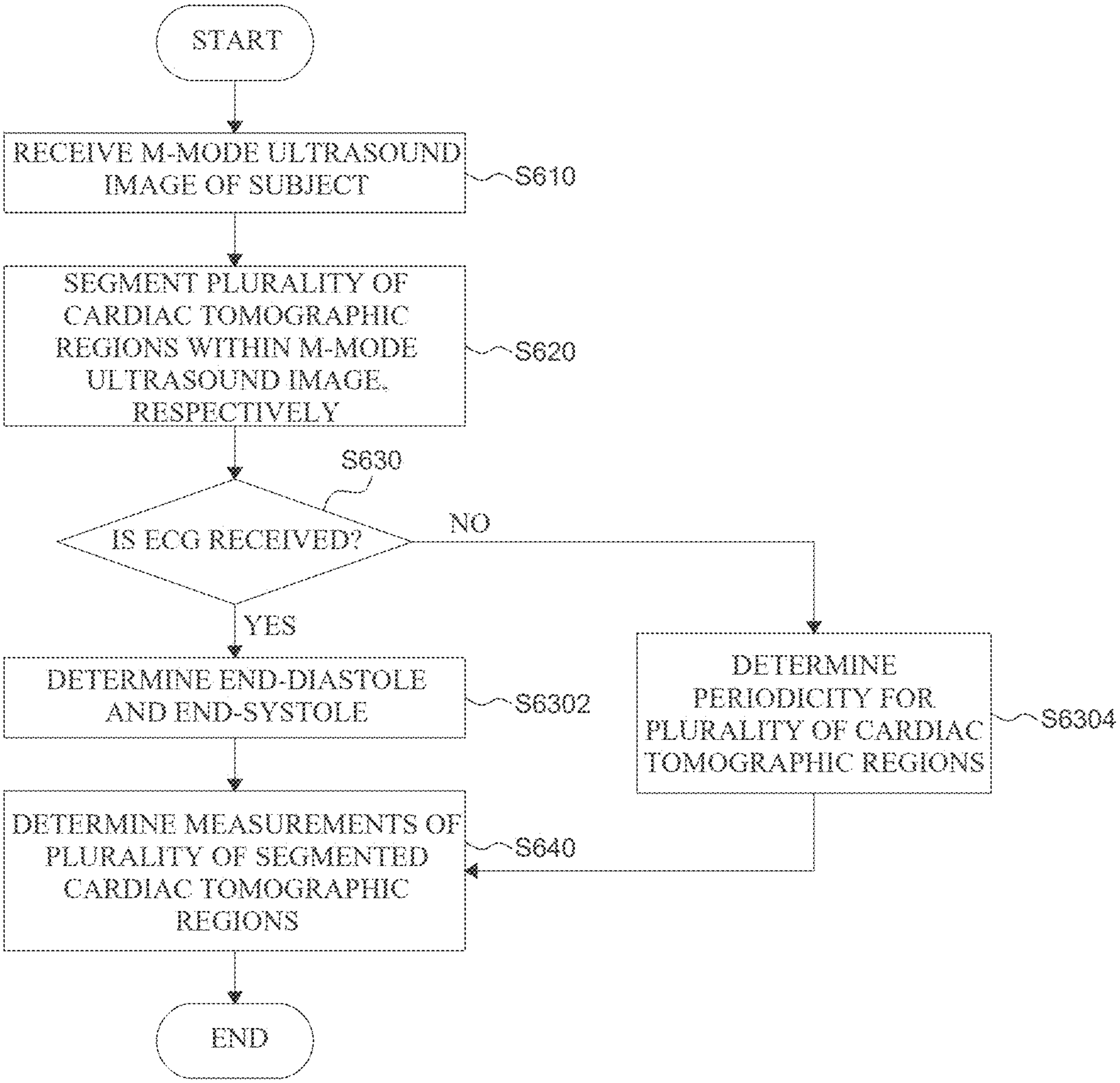
FIG. 6 exemplarily illustrates a process of a method for providing information on an M-mode ultrasound image according to yet another embodiment of the present invention.

FIG. 3 illustrates a process of a method for providing information on an M-mode ultrasound image according to an embodiment of the present invention. FIG. 4 exemplarily illustrates a process of a method for providing information on an M-mode ultrasound image according to an embodiment of the present invention. FIGS. 5A and 5B exemplarily illustrate a process of a method for providing information on an M-mode ultrasound image according to another embodiment of the present invention. FIG. 6 exemplarily illustrates a process of a method for providing information on an M-mode ultrasound image according to yet another embodiment of the present invention.

First, referring to FIG. 3, an information provision process according to one embodiment of the present invention is as follows. First, an M-mode ultrasound image of a subject is received (S310). Next, a plurality of cardiac tomographic regions are segmented by a segmentation model (S320). Next, measurements are determined based on the segmented cardiac tomographic regions (S330).

More specifically, in step (S310) where the M-mode ultrasound image is received, an M-mode ultrasound image of a target area, i.e., a heart area, may be received.

According to a feature of the present invention, in step (S310) where the M-mode ultrasound image is received, an M-mode ultrasound image cropped with the M-mode region may be received. That is, before step (S310) in which the M-mode ultrasound image is received, cropping for an essential area for segmenting the M-mode ultrasound image may be performed.

Next, step (S320) is performed in which the cardiac tomographic regions are segmented.

According to a feature of the present invention, in step (S320) in which the cardiac tomographic regions are segmented, in the M-mode ultrasound image, at least two regions selected from the RV anterior wall, the right ventricle (RV), the anterior wall of aorta, the aorta, the posterior wall of aorta, the left atrium (LA), and the posterior wall of LA are segmented by the segmentation model.

According to another feature of the present invention, in step (S320) in which the cardiac tomographic regions are segmented, at least two regions selected from the RV anterior wall, the right ventricle, the interventricular septum (IVS), the left ventricle (LV), and the LV posterior wall are segmented by the segmentation model. However, it is not limited thereto, and more diverse regions may also be segmented depending on a type of M-mode.

According to yet another feature of the present invention, after step (S320) in which the cardiac tomographic regions are segmented, post-processing may be further performed.

Figure 7:
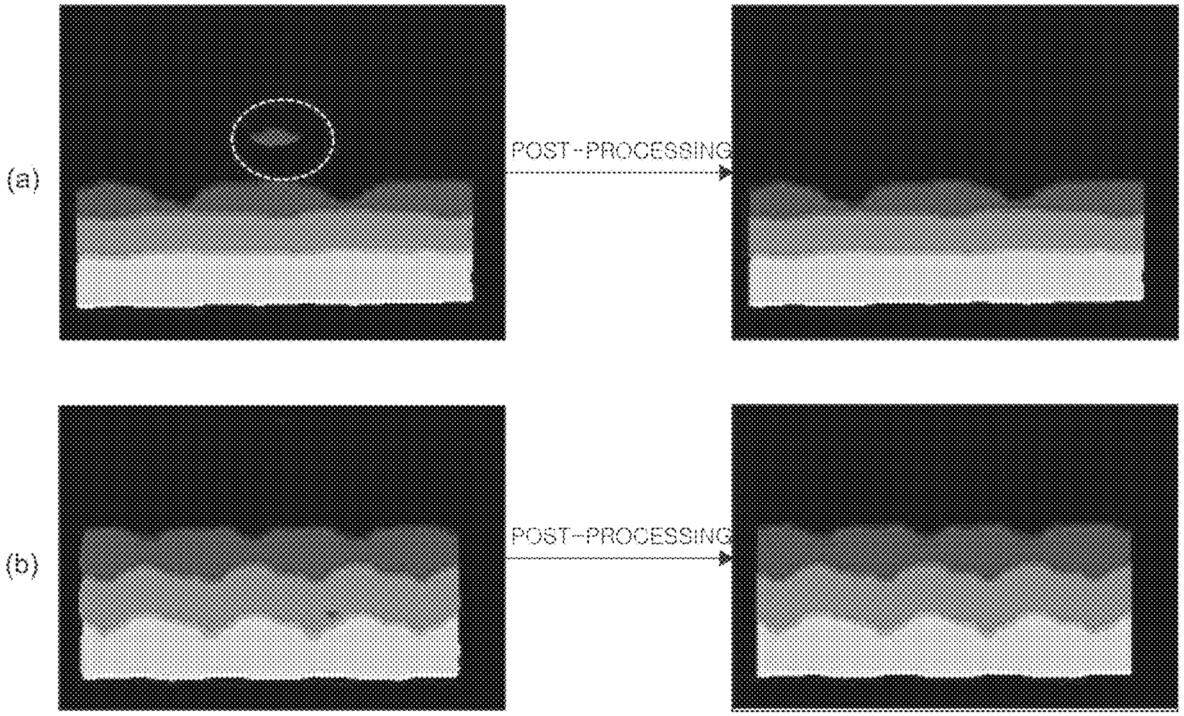
FIG. 7 exemplarily illustrates a post-correction process of a method for providing information on an M-mode ultrasound image according to various embodiments of the present invention.

For example, referring to FIGS. 7A and 7B, post-processing may be further performed, such as removing the segmented regions other than the M-mode region, filling holes within the segmented regions, and the like.

Meanwhile, according to yet another feature of the present invention, after step (S320) in which the cardiac tomographic regions are segmented, an electrocardiogram (ECG) for the subject is received, and end-diastole and end-systole may be determined based on the ECG.

Next, in step (S330) where the measurements is determined, the measurements are determined based on the end-diastole and the end-systole.

For example, referring to FIG. 4 together, in step (S320) in which the cardiac tomographic regions are segmented, when an M-mode ultrasound image 412 is input into a segmentation model 420, a plurality of cardiac tomographic regions 422 are output. Next, the electrocardiogram (ECG) data 432 for the subject is received, and end-diastole (ED) and end-systole (ES) periods 434 are determined for the plurality of cardiac tomographic regions 422 based on the ECG data 432. Next, in step (S330) where the measurements are determined, measurements (e.g., aorta diameter, LA diameter, IVS diameter, LV internal diameter (LVID), or LV posterior wall diameter) are automatically determined based on the end-diastole and the end-systole.

However, the determination of the measurements is not limited thereto, and the measurements may be determined only from the segmented cardiac tomographic regions.

According to yet another feature of the present invention, after step (S320) in which the cardiac tomographic regions are segmented, periodicity for the plurality of cardiac tomography regions is determined.

Here, the periodicity may be determined based on peaks by calculating the degree of auto-correlation for the plurality of cardiac tomographic regions, and determining peaks based on the degree of auto-correlation.

However, it is not limited thereto, and the periodicity may also be determined by calculating the degree of cross-correlation for adjacent regions of the plurality of cardiac tomographic regions and determining peaks based on the degree of cross-correlation.

Next, in step (S330) where the measurements are determined, the measurements are determined based on the periodicity of the determined cardiac tomographic regions.

For example, referring to FIG. 5A together, in step (S320) in which the cardiac tomographic regions are segmented, when the M-mode ultrasound image 412 is input into the segmentation model 420, the plurality of cardiac tomographic regions 422 are output. Next, the auto-correlation of each of the plurality of cardiac tomographic regions 422 is calculated and then the peaks are detected. As a result, periodicity 436 may be detected. That is, measurements 442 may be determined based on the periodicity 436 without determining end-diastole and end-systole based on the ECG.

Optionally, the measurements may also be determined by determining a plurality of local maxima and a plurality of local minima 437 for the segmented regions, or by calculating a gradient 438 for the segmented regions.

That is, the determination of the measurements may be performed by at least one of processes of determining periodicity, determining local maxima and local minima, and calculating the gradient.

For example, referring further to FIG. 5B, after the gradient is calculated, specific points whose gradient is close to 0 are determined, and then the determined specific points may be clustered.

At this time, in step (S330) where the measurements are determined, measurements (e.g., aorta diameter, LA diameter, IVS diameter, LV internal diameter (LVID), or LV posterior wall diameter) are automatically determined based on at least one of the determined peaks, local maxima, local minima, and gradient.

Therefore, when it is difficult to obtain ECG data, automatic determination of measurements may be possible using only the M-mode ultrasound image.

In other words, it is possible to obtain M-mode-based measurements even in secondary and tertiary hospitals where it is difficult to obtain ECG data, by providing an information provision system with different methods for determining measurements depending on presence or absence of ECG.

Meanwhile, according to a feature of the present invention, after step (S330) in which the measurements are determined, an entropy value is determined, and the measurements may be verified based on the entropy value.

For example, when an entropy value corresponding to uncertainty is a predetermined level or more, the measurements thereof may be excluded.

Accordingly, a medical staff may easily identify measurements from the obtained M-mode ultrasound image according to the information provision method according to various embodiments of the present invention, thereby quickly performing an ultrasound analysis step and establishing more accurate decision-making and treatment plans.

Meanwhile, the information provision method according to various embodiments of the present invention is not limited to the above-described process.

For example, referring to FIG. 6, step (S630) of selectively receiving ECG data is performed, and when the ECG is received, step (S6302) of determining end-diastole and end-systole based on the ECG is performed, and measurements are determined based thereon (S640). Meanwhile, when the ECG is not received, step (S6304) of determining the periodicity for the plurality of cardiac tomographic regions is performed, and measurements are determined based on the periodicity (S640). The process of FIG. 6 includes a step S610 and a step S620 that may be correlative to the steps S310 and S320 of FIG. 3, respectively.

That is, depending on whether the ECG data is received or not, a process of determining more diverse measurements may be performed.

Hereinafter, a segmentation model and measurements used in various embodiments of the present invention will be described with reference to FIGS. 8A to 8D.

Figure 8A:
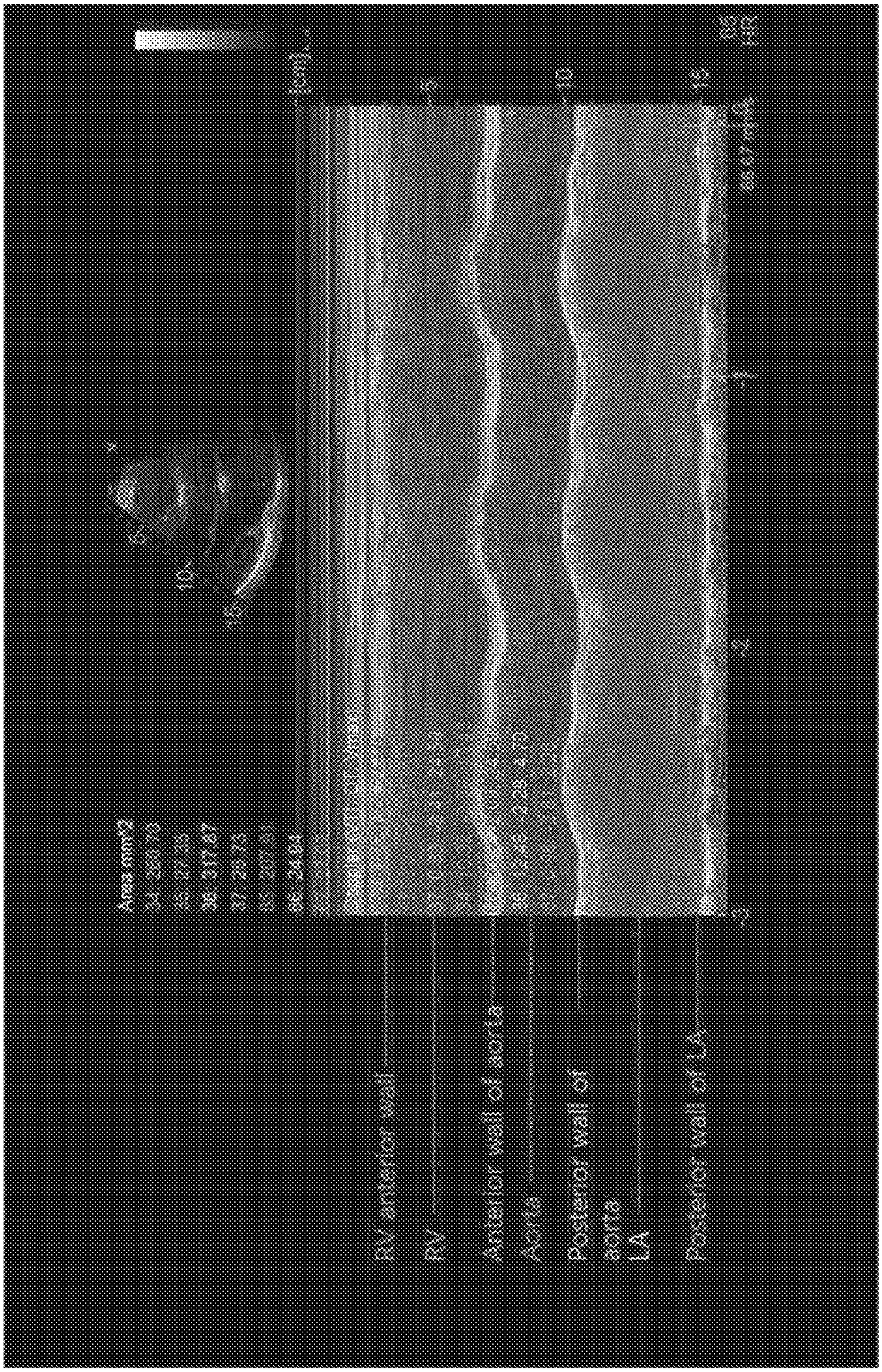
FIGS. 8A and 8B exemplarily illustrate training data of a segmentation model used in various embodiments of the present invention.
Figure 8B:
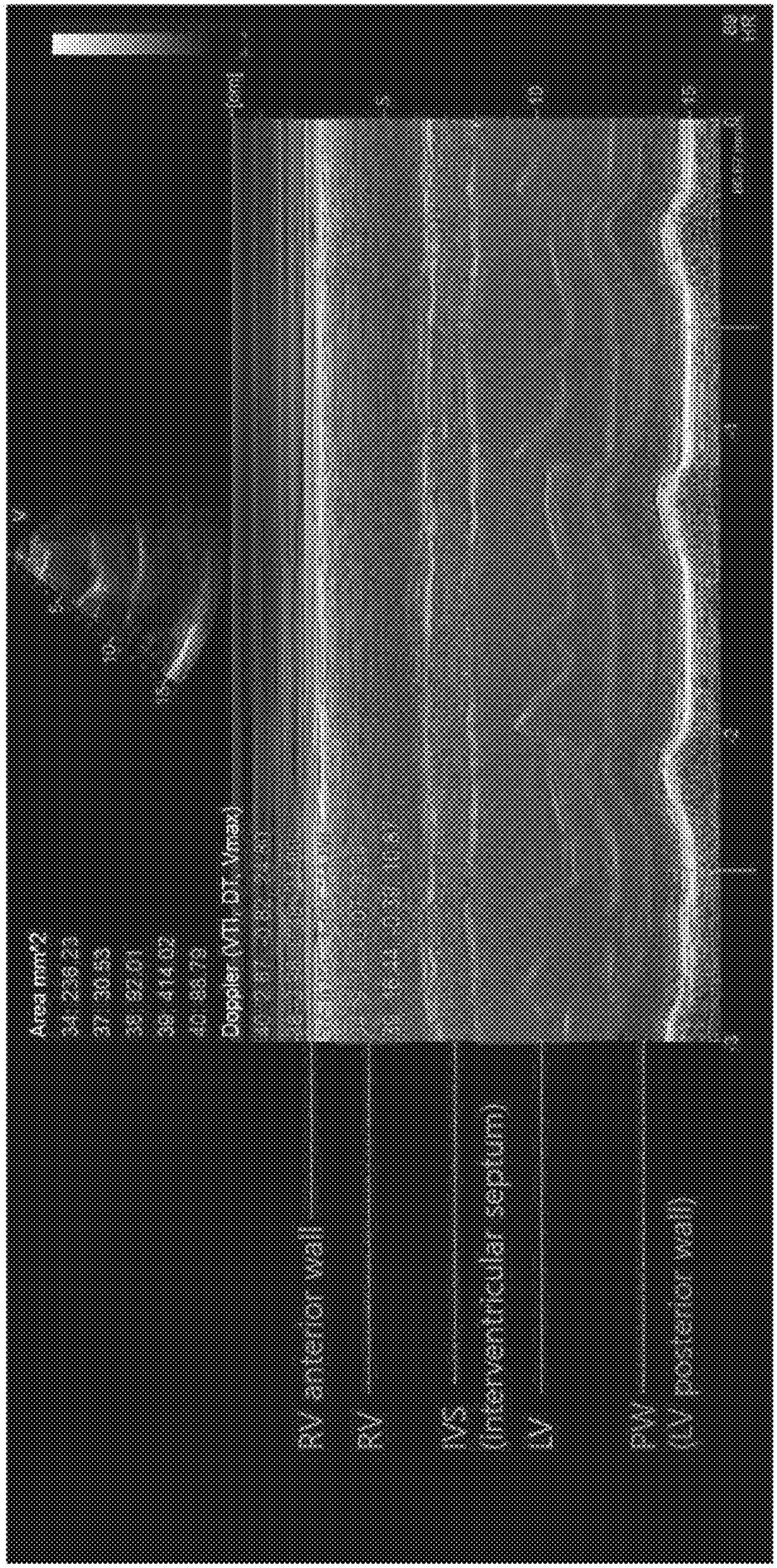
Figure 8C:
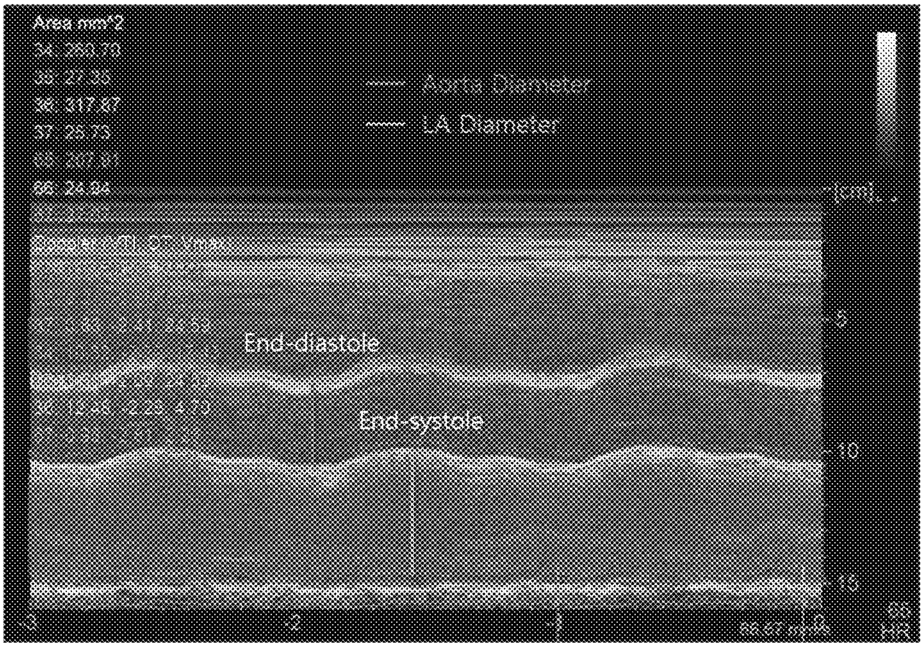
FIGS. 8C and 8D exemplarily illustrate measurements determined in a method for providing information on an M-mode ultrasound image according to various embodiments of the present invention.
Figure 8D:
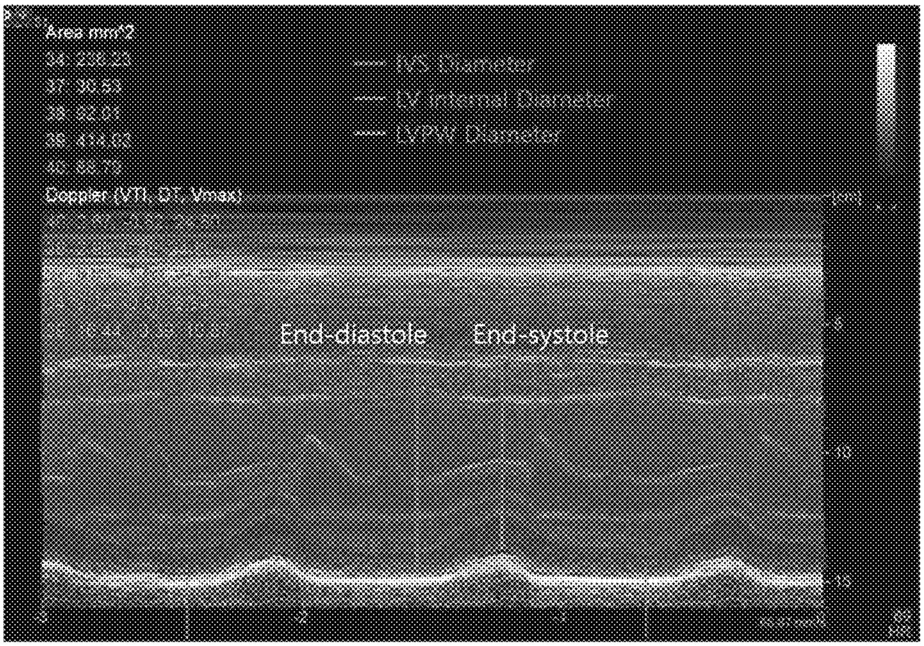

FIGS. 8A and 8B exemplarily illustrate training data of a segmentation model used in various embodiments of the present invention. FIGS. 8C and 8D exemplarily illustrate measurements determined in a method for providing information on an M-mode ultrasound image according to various embodiments of the present invention.

First, referring to FIG. 8A, a segmentation model may use an M-mode ultrasound image for training, which is labeled with seven regions of the RV anterior wall, the right ventricle, the anterior wall of aorta, the aorta, the posterior wall of aorta, the left atrium, and the posterior wall of LA.

That is, the segmentation model may be a model trained to segment the regions for left atrium-aorta (LA-Ao) analysis.

Next, referring further to FIG. 8B, the segmentation model may use an M-mode ultrasound image for training, which is labeled with five regions of the RV anterior wall, the right ventricle, the interventricular septum, the left ventricle, and the LV posterior wall.

That is, the segmentation model may be a model trained to segment the regions for left ventricle (LV) analysis.

Meanwhile, the M-mode image for training is not limited thereto, and the labeling regions may vary depending on a region to be segmented and a analysis goal.

Next, referring to FIG. 8C, the measurements may be an LA diameter corresponding to systole and an aorta diameter corresponding to end-diastole.

Referring further to FIG. 8D, the measurements may be an interventricular septum (IVS) diameter, an LV internal diameter (LVID), and an LV posterior wall (LVPW) diameter corresponding to each of end-systole and end-diastole.

However, the measurements are not limited to those described above and may be set more diversely depending on an analysis goal.

Evaluation 1: Evaluation Results for Measurements

Hereinafter, evaluation results for measurements determined according to an information provision method according to various embodiments of the present invention will be described with reference to FIGS. 9A to 9F.

First, referring to FIG. 9A, in left atrium-aorta analysis, correlation coefficients between measurements manually determined by experts and measurements automatically determined according to an information provision method according to various embodiments of the present invention are illustrated.

Figure 9B:
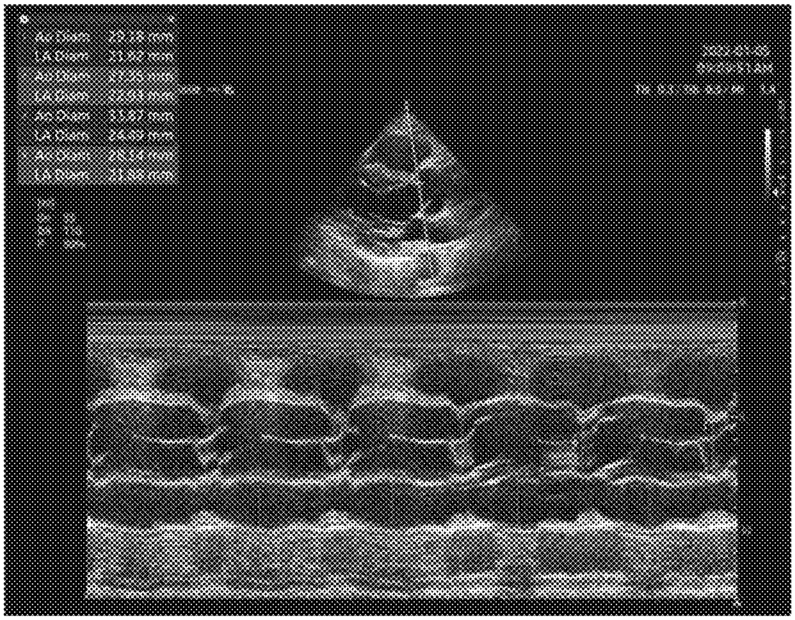
Figure 9B:
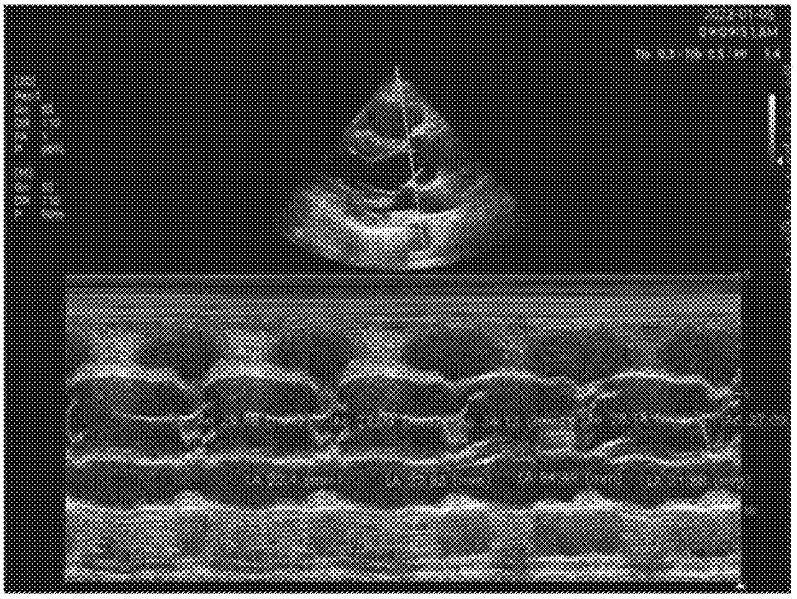
Figure 9C:
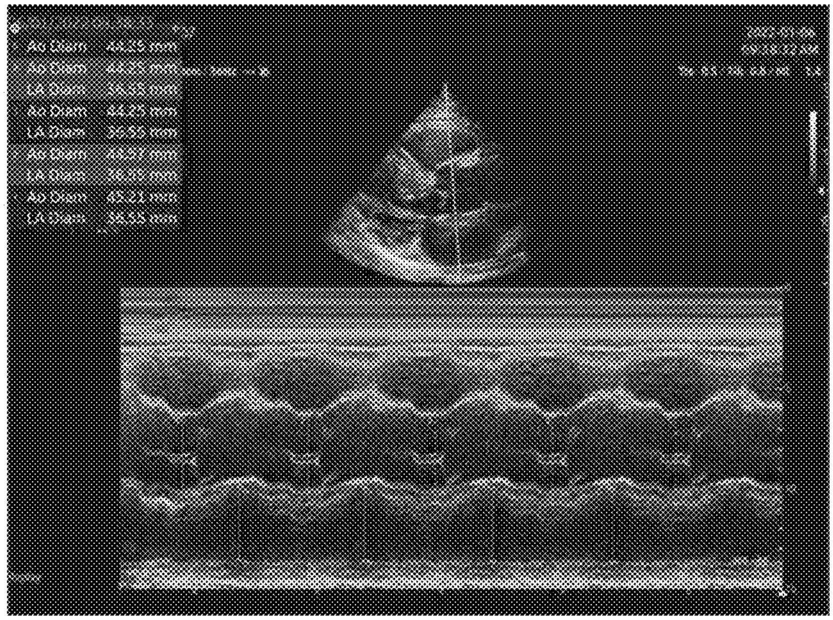
Figure 9C:
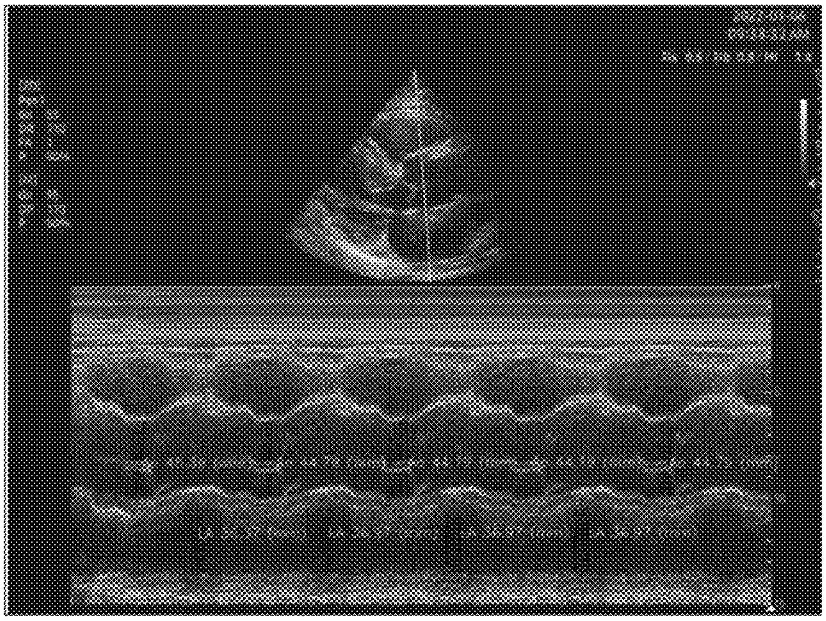

More specifically, referring to FIGS. 9B and 9C together, a correlation coefficient for the measurements of the LA diameter is 0.91, and a correlation coefficient for the measurements of the aorta diameter is 0.97, which has a high correlation with the measurements by experts.

These results may imply that there is high clinical reliability of measurements determined according to the information provision method according to various embodiments of the present invention.

Next, referring to FIG. 9D, in left ventricle analysis, correlation coefficients between measurements manually determined by experts and measurements automatically determined according to the information provision method according to various embodiments of the present invention are illustrated.

Figure 9E:
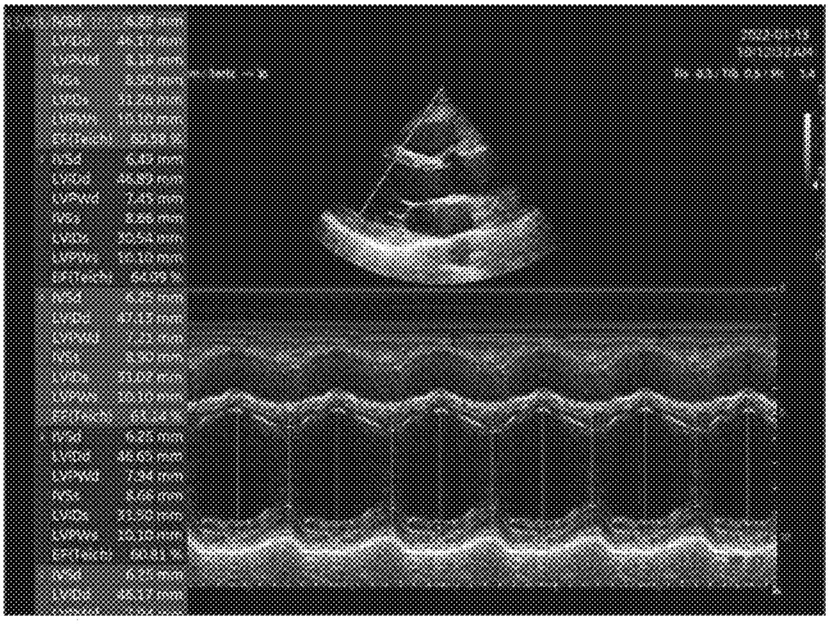
Figure 9E:
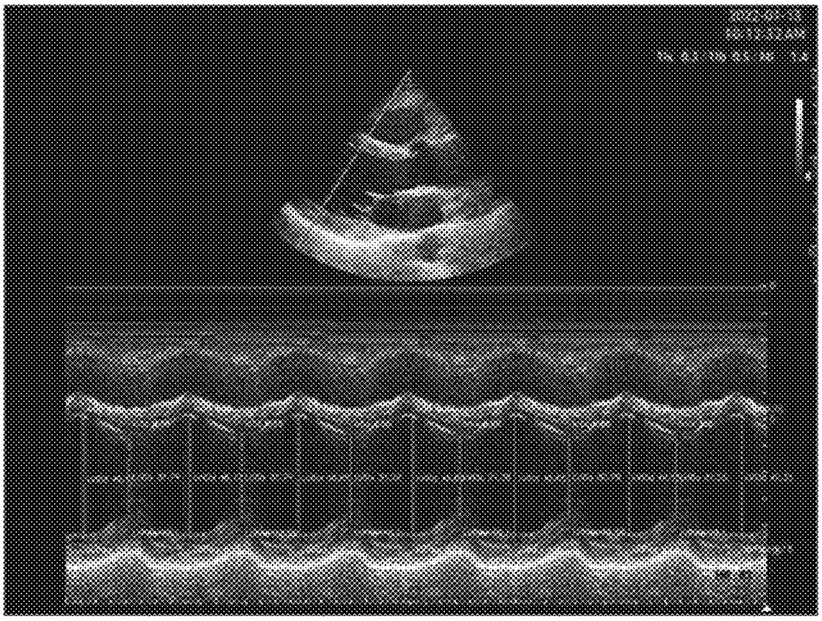
Figure 9F:
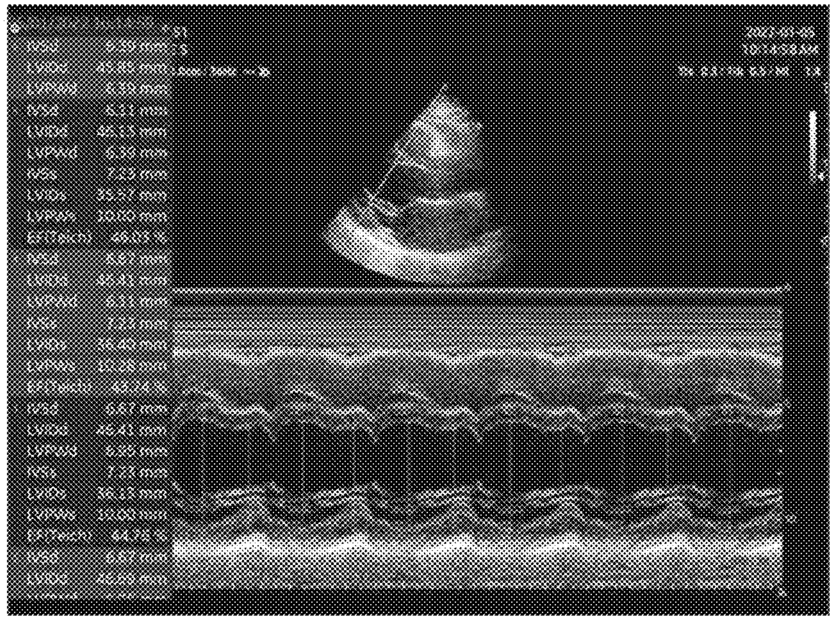
Figure 9F:
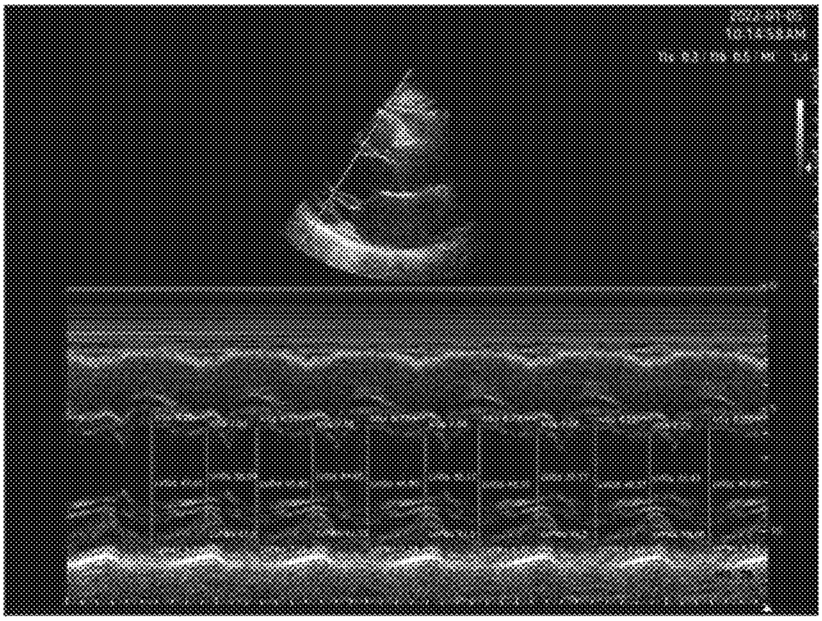

More specifically, referring to FIGS. 9E and 9F together, a correlation coefficient for the IVS diameter at end-diastole is 0.93, a correlation coefficient for the LV internal diameter at end-diastole is 0.95, and a correlation coefficient for the LV posterior wall diameter at end-diastole is 0.81.

Furthermore, a correlation coefficient for the IVS diameter at end-systole is 0.80, a correlation coefficient for the LV internal diameter at end-systole is 0.97, and a correlation coefficient for the LV posterior wall diameter at end-systole is 0.85.

These results may imply that the measurements determined by the information provision method according to various embodiments of the present invention have a high correlation with the measurements by experts, and furthermore, have high clinical reliability.

That is, according to the present invention, it is possible to provide highly reliable analysis results for M-mode ultrasound images regardless of the skill level of medical staff, and to contribute to establishing more accurate decision-making and treatment plans at an image analysis step.

Furthermore, according to the present invention, it is possible to obtain M-mode-based measurements even in secondary and tertiary hospitals where it is difficult to obtain ECG data, by providing an information provision system with different methods for determining measurements depending on presence or absence of ECG.

Figure 10:
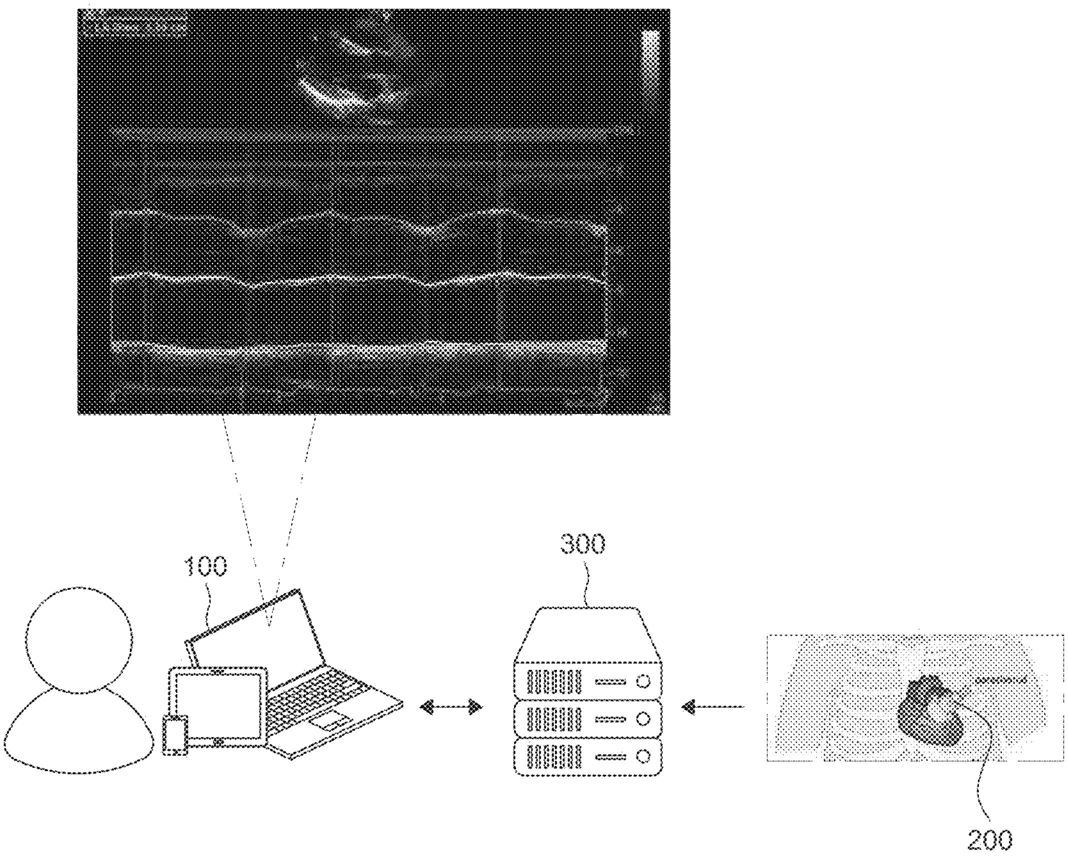
FIG. 10 is a schematic diagram of a system for providing information on an M-mode ultrasound image using a device for providing information on an M-mode ultrasound image according to an embodiment of the present invention.

FIG. 10 is a schematic diagram of a system for providing information on an M-mode ultrasound image using a device for providing information on an M-mode ultrasound image according to an embodiment of the present invention.

Referring to FIG. 10, a system for providing information on an M-mode ultrasound image includes a medical staff device 100, an ultrasound image diagnosis device 200, and a user interface provision server 300 (hereinafter, an information provision server 300 for an M-mode ultrasound image).

The system for providing information on the M-mode ultrasound image may provide information related to an M-mode ultrasound image based on the M-mode ultrasound image of a subject. At this time, the system for providing information on the M-mode ultrasound image may be configured by a medical staff device 100 that receives information associated with an M-mode ultrasound image, an ultrasound image diagnosis device 200 that provides an M-mode ultrasound image, and an information provision server 300 that generates information on an M-mode ultrasound image based on the received M-mode ultrasound image.

Figure 11:
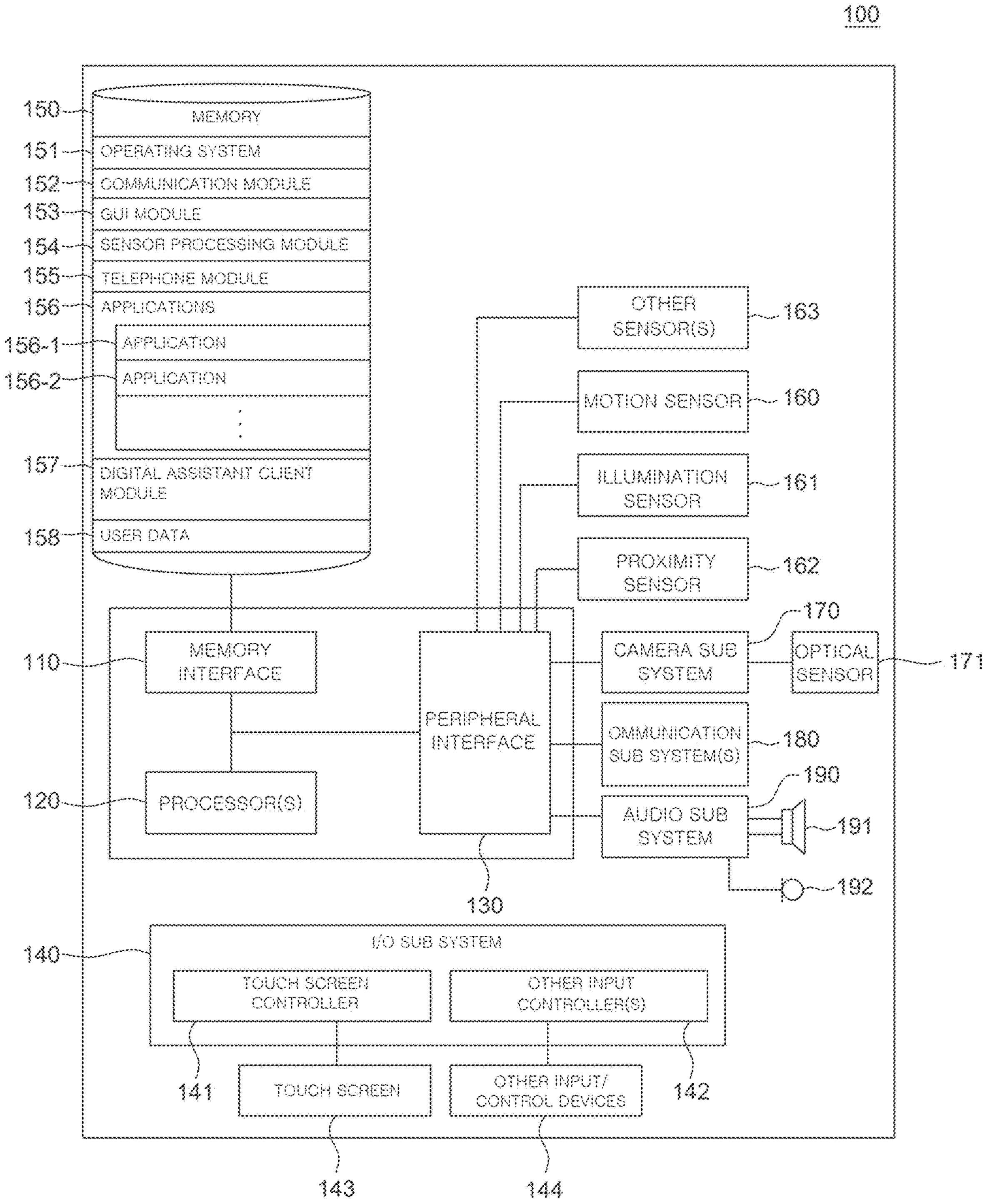
FIG. 11 is a block diagram illustrating a configuration of a medical staff device according to an embodiment of the present invention.

Specifically, the medical staff device 100 may be a device that provides a user interface for exposing information related to the M-mode ultrasound image. At this time, the medical staff device 100 may receive prediction results associated with the M-mode ultrasound image of the subject from the server 300 for providing the information on the M-mode ultrasound image, and display the received results. Here, the medical staff device 100 is an electronic device capable of capturing and outputting images, and may include a smartphone, a tablet PC, a PC, a laptop computer, etc. FIG. 11 is a block diagram illustrating a configuration of a medical staff device according to an embodiment of the present invention.

Referring to FIG. 11, a medical staff device 100 may include a memory interface 110, one or more processors 120, and a peripheral interface 130. Various components in the medical staff device 100 may be connected to each other by one or more communication buses or signal lines.

The memory interface 110 is connected to the memory 150 to transmit various data to the processors 120. Here, the memory 150 may include at least one type of storage medium of a flash memory type, a hard disk type, a multimedia card micro type, a card type memory (e.g., SD or XD memory, etc.), a RAM, an SRAM, a ROM, an EEPROM, a PROM, a network storage, a cloud, and a blockchain database.

In various exemplary embodiments, the memory 150 may store at least one or more of an operating system 151, a communication module 152, a graphical user interface (GUI) module 153, a sensor processing module 154, a phone module 155 and an application module 156. Specifically, the operating system 151 may include instructions for processing a basic system service and instructions for performing hardware operations. The communication module 152 may communicate with at least one of other one or more devices, computers and servers. The GUI module 153 may process a graphical user interface. The sensor processing module 154 may process sensor-related functions (e.g., processing a received voice input using one or more microphones 192). The phone module 155 may process phone-related functions. The application module 156 may perform various functions of the user application, such as electronic messaging, web browsing, media processing, searching, imaging, and other process functions. Further, the medical staff device 100 may store one or more software applications 156-1 and 156-2 associated with any one type of service in the memory 150. At this time, the application 156-1 may provide information on the M-mode ultrasound image to the medical staff device 100.

In various embodiments, the memory 150 may store a digital assistant client module 157 (hereinafter, referred to as a DA client module), and accordingly, may store instructions to perform client-side functions of a digital assistant and various user data 158 (e.g., other data, such as user-tailored vocabulary data, preference data, user's electronic address book, to-do list, shopping list, etc.).

On the other hand, the DA client module 157 may acquire a voice input, a text input, a touch input and/or a gesture input of the user through various user interfaces (e.g., an I/O subsystem 140) provided in the medical staff device 100.

In addition, the DA client module 157 may output audio-visual and tactile types of data. For example, the DA client module 157 may output data consisting of combinations of at least two or more of voice, sound, notifications, text messages, menus, graphics, video, animation, and vibration.

In addition, the DA client module 157 may communicate with a digital assistant server (not illustrated) using a communication subsystem 180.

In various exemplary embodiments, the DA client module 157 may collect additional information on a surrounding environment of the medical staff device 100 from various sensors, subsystems and peripheral devices in order to configure a context associated with the user input. For example, the DA client module 157 may infer a user's intention by providing context information with the user input to the digital assistant server. Here, the context information that may be accompanied by the user input may include sensor information, for example, lighting, ambient noise, ambient temperature, images and videos in an ambient environment, and the like. For another example, the context information may include physical states of the medical staff device 100 (e.g., device orientation, device location, device temperature, power level, speed, acceleration, motion pattern, cellular signal strength, etc.). For yet another example, the context information may include information related to software states of the medical staff device 100 (e.g., processes running on the medical staff device 100, installed programs, previous and current network activities, background services, error logs, resource usage, etc.).

In various exemplary embodiments, the memory 150 may include added or deleted instructions, and furthermore, the medical staff device 100 may include additional configurations in addition to the configurations illustrated in FIG. 11, or may also exclude some configurations.

The processor 120 may control the overall operation of the medical staff device 100 and execute various instructions to implement an interface that provides information related to M-mode ultrasound imaging by driving applications or programs stored in the memory 150.

The processor 120 may correspond to a computing device such as a central processing unit (CPU) or an application processor (AP). In addition, the processor 120 may be implemented in the form of an integrated chip (IC), such as a system on chip (SoC) integrated with various computing devices such as a neutral processing unit (NPU).

The peripheral interface 130 is connected with various sensors, subsystems and peripheral devices to provide data so that the medical staff device 100 may perform various functions. Here, it may be understood that whether the medical staff device 100 performs any function is performed by the processor 120.

The peripheral interface 130 may receive data from a motion sensor 160, a lighting sensor (optical sensor) 161 and a proximity sensor 162, so that the medical staff device 100 may perform orientation, lighting, and proximity sensing functions, etc. For another example, the peripheral interface 130 may receive data from other sensors 163 (positioning system-GPS receiver, temperature sensor, and biometric sensor), so that the medical staff device 100 may perform functions associated with other sensors 163.

In various exemplary embodiments, the medical staff device 100 may include a camera subsystem 170 connected with the peripheral interface 130 and an optical sensor 171 connected thereto, so that the medical staff device 100 may perform various photographing functions such as photographing, video clip recording, etc.

In various exemplary embodiments, the medical staff device 100 may include a communication subsystem 180 connected with the peripheral interface 130. The communication subsystem 180 is configured as one or more wired/wireless networks, and may include various communication ports, radio frequency transceivers, and optical transceivers.

In various exemplary embodiments, the medical staff device 100 includes an audio subsystem 190 connected with the peripheral interface 130, and the audio subsystem 190 includes one or more speakers 191 and one or more microphones 192, so that the medical staff device 100 may perform a voice-operating function, such as voice recognition, voice reproduction, digital recording, and phone functions, etc.

In various exemplary embodiments, the medical staff device 100 may include an I/O subsystem 140 connected with the peripheral interface 130. For example, the I/O subsystem 140 may control a touch screen 143 included in the medical staff device 100 through a touch screen controller 141. As an example, the touch screen controller 141 may detect contact and motion of the user or interruption of the contact and motion by using any one of a plurality of touch sensing techniques, such as capacitive, resistive, infrared, and surface elastic wave techniques, proximity sensor arrays, etc. For another example, the I/O subsystem 140 may control other input/control devices 144 included in the medical staff device 100 through other input controller(s) 142. As an example, the other input controller(s) 142 may control a pointer device, such as one or more buttons, rocker switches, thumb-wheels, infrared ports, USB ports, and styluses.

Figure 12:
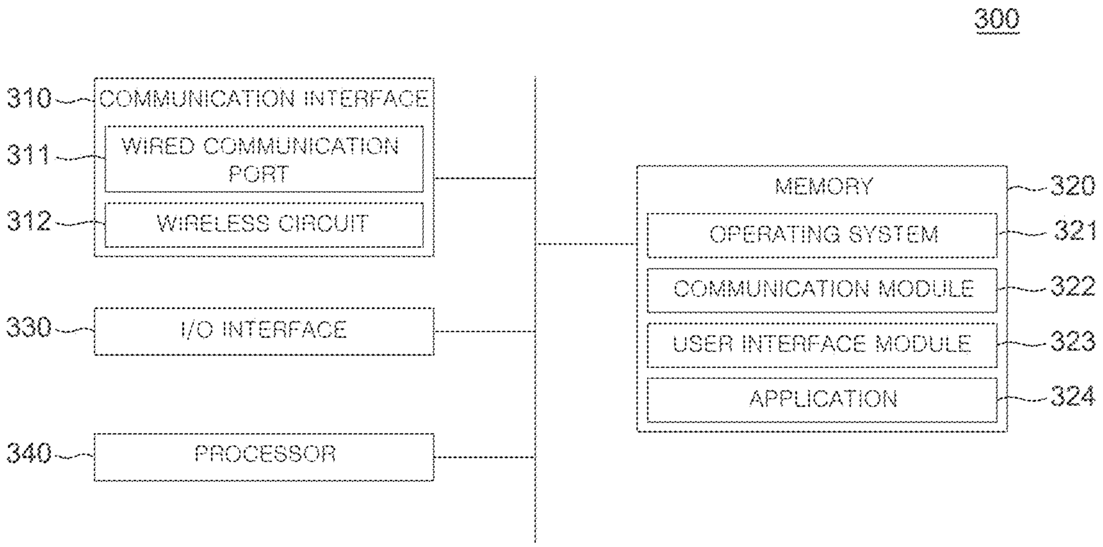
FIG. 12 is a block diagram illustrating a configuration of an information provision server according to an embodiment of the present invention.

FIG. 12 is a block diagram illustrating a configuration of an information provision server according to an embodiment of the present invention.

Referring to FIG. 12, the information provision server 300 for the M-mode ultrasound image may include a communication interface 310, a memory 320, and an I/O interface 330, which may communicate with each other through one or more communication buses or signal lines.

The communication interface 310 is connected with the medical staff device 100 and the ultrasound image diagnosis device 200 through a wired/wireless communication network to transmit and receive data. For example, the communication interface 310 may receive an M-mode ultrasound image from the ultrasound image diagnosis device 200. At this time, the communication interface 310 may transmit information associated with measurements determined from the M-mode ultrasound image to the medical staff device 100.

Meanwhile, the communication interface 310 to transmit and receive such data includes a communication port 311 and a wireless circuit 312, in which the wired communication port 311 may include one or more wired interfaces, such as Ethernet, a universal serial bus (USB), a firewire, and the like. In addition, the wireless circuit 312 may transmit and receive data with an external device through an RF signal or an optical signal. In addition, the wireless communication may use at least one of a plurality of communication standards, protocols and technologies, such as GSM, EDGE, CDMA, TDMA, Bluetooth™ wireless communication protocol, Wi-Fi™ wireless local area network communication, VOIP, and Wi-MAX, or any other suitable communication protocols.

The memory 320 may store various data used in the information provision server 300 for the M-mode ultrasound image. For example, the memory 320 may store an M-mode ultrasound image. At this time, the memory 320 may store a first model trained to segment cardiac tomographic regions within the M-mode ultrasound image. In addition, the memory 320 may store a second model trained to predict diastole and systole within the M-mode ultrasound image.

In various exemplary embodiments, the memory 320 may include a volatile or nonvolatile recording medium capable of storing various data, instructions, and information. For example, the memory 320 may include at least one type of storage medium of a flash memory type, a hard disk type, a multimedia card micro type, a card type memory (e.g., an SD or XD memory, etc.), a RAM, an SRAM, a ROM, an EEPROM, a PROM, a network storage, a cloud, and a blockchain database.

In various exemplary embodiments, the memory 320 may store at least one configuration of an operating system 321, a communication module 322, a user interface module 323, and one or more applications 324.

The operating system 321 (e.g., embedded operating system such as LINUX, UNIX, MAC™ operating system, Windows™ operating system, VxWorks, etc.) may include various software components and drivers for controlling and managing general system operations (e.g., memory management, storage device control, power management, etc.), and may support communication among various hardware, firmware, and software components.

The communication module 323 may support communication with other devices through the communication interface 310. The communication module 320 may include various software components for processing the data received by the wired communication port 311 or the wireless circuit 312 of the communication interface 310.

The user interface module 323 may receive a request or input of the user from a keyboard, a touch screen, a microphone, etc. through the I/O interface 330, and may provide a user interface on the display.

The application 324 may include a program or module that is configured to be executed by one or more processors 340. Here, the application for providing information on the M-mode ultrasound image may be implemented on a server farm.

The I/O interface 330 may connect at least one of I/O devices (not illustrated) of the information provision server 300 for the M-mode ultrasound image, for example, at least one of a display, a keyboard, a touch screen and a microphone, with the user interface module 323. The I/O interface 330 may receive a user input (e.g., voice input, keyboard input, touch input, etc.) with the user interface module 323, and process instructions according to the received input.

The processor 340 is connected with the communication interface 310, the memory 320, and the I/O interface 330 to control the overall operation of the information provision server 300 for the M-mode ultrasound image, and may perform various instructions for providing information on the M-mode ultrasound image through applications or programs stored in the memory 320.

The processor 340 may correspond to a computing device such as a central processing unit (CPU) or an application processor (AP). In addition, the processor 340 may be implemented in the form of an integrated chip (IC), such as a system on chip (SoC) integrated with various computing devices. Alternatively, the processor 340 may include a module for calculating an artificial neural network model, such as a neural processing unit (NPU).

In various exemplary embodiments, the processor 340 may receive an M-mode ultrasound image of a subject from the ultrasound image diagnosis device 200. At this time, the subject may target a patient's heart.

The processor 340 may segment a plurality of cardiac tomographic regions within the M-mode ultrasound image, respectively. At this time, the processor 340 may use a first model trained to segment the plurality of cardiac tomographic regions by inputting the M-mode ultrasound image. Here, the plurality of cardiac tomographic regions may be at least two regions selected from the right ventricle anterior wall, the right ventricle (RV), the anterior wall of aorta, the aorta, the posterior wall of aorta, the left atrium (LA), and the posterior wall of LA. As another example, the plurality of cardiac tomographic regions may be at least two regions selected from the RV anterior wall, the right ventricle, the interventricular septum (IVS), the left ventricle (LV), and the LV posterior wall.

The processor 340 may predict diastole and systole within the M-mode ultrasound image. At this time, the processor 340 may use a second model trained to predict diastole and systole in the M-mode ultrasound image by inputting the M-mode ultrasound image. Here, the second model may be a model that predicts end-diastole and end-systole of the M-mode ultrasound image. As another example, the second model may be a model that predicts each period of diastole and systole of the M-mode ultrasound image.

The processor 340 may provide measurements of the plurality of segmented cardiac tomographic regions to the medical staff device 100. At this time, the processor 340 may determine measurements for the plurality of segmented cardiac tomographic regions based on the diastole and systole predicted from the second model. Here, the processor 340 may determine measurements for the plurality of cardiac tomographic regions based on the end-diastole and end-systole provided from the second model. As another example, the processor 340 may determine measurements for the plurality of cardiac tomographic regions at transition points of each period of the diastole and systole based on each period of the diastole and systole provided from the second model.

So far, the configuration of the information provision server 300 for the M-mode ultrasound image according to an embodiment of the present invention has been described. Hereinafter, a method for providing information on an M-mode ultrasound image through the information provision server 300 for the M-mode ultrasound image described above will be described.

Figure 13:
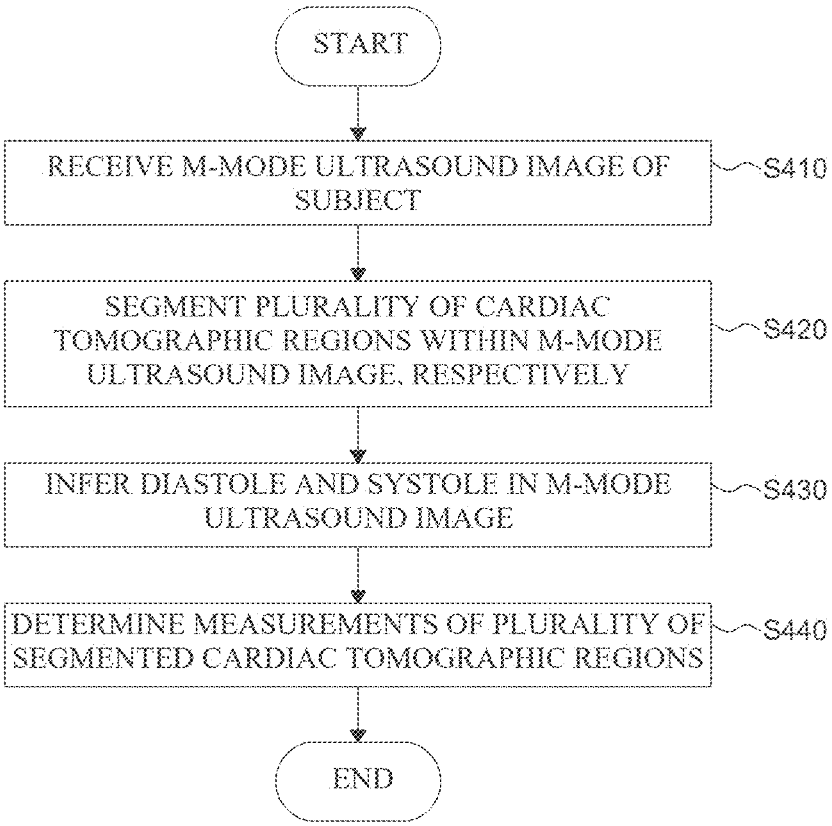
FIG. 13 is a flowchart of a method for providing information on an M-mode ultrasound image according to an embodiment of the present invention.

FIG. 13 is a flowchart of a method for providing information on an M-mode ultrasound image according to an embodiment of the present invention and FIGS. 14 to 19D are exemplary diagrams of a method for providing information on an M-mode ultrasound image according to an embodiment of the present invention.

First, referring to FIG. 13, the information provision server 300 for the M-mode ultrasound image receives an M-mode ultrasound image of at least one subject from the ultrasound image diagnosis device 200 (S410). At this time, the information provision server 300 for the M-mode ultrasound image may receive an M-mode ultrasound image for a patient's heart from the ultrasound image diagnosis device 200. Here, the information provision server 300 for the M-mode ultrasound image may receive an M-mode ultrasound image cropped with an M-mode region. At this time, the information provision server 300 for the M-mode ultrasound image may perform cropping for an essential area for segmenting the M-mode ultrasound image.

The information provision server 300 for the M-mode ultrasound image segments a plurality of cardiac tomographic regions within the M-mode ultrasound image, respectively (S420). At this time, the information provision server 300 for the M-mode ultrasound image may use a first model trained to segment the plurality of cardiac tomographic regions by inputting the M-mode ultrasound image. Here, the plurality of cardiac tomographic regions may be at least two regions selected from the right ventricle anterior wall, the right ventricle (RV), the anterior wall of aorta, the aorta, the posterior wall of aorta, the left atrium (LA), and the posterior wall of LA. As another example, the plurality of cardiac tomographic regions may be at least two regions selected from the RV anterior wall, the right ventricle, the interventricular septum (IVS), the left ventricle (LV), and the LV posterior wall. However, it is not limited thereto, and more diverse regions may also be segmented depending on a type of M-mode.

Figure 14:
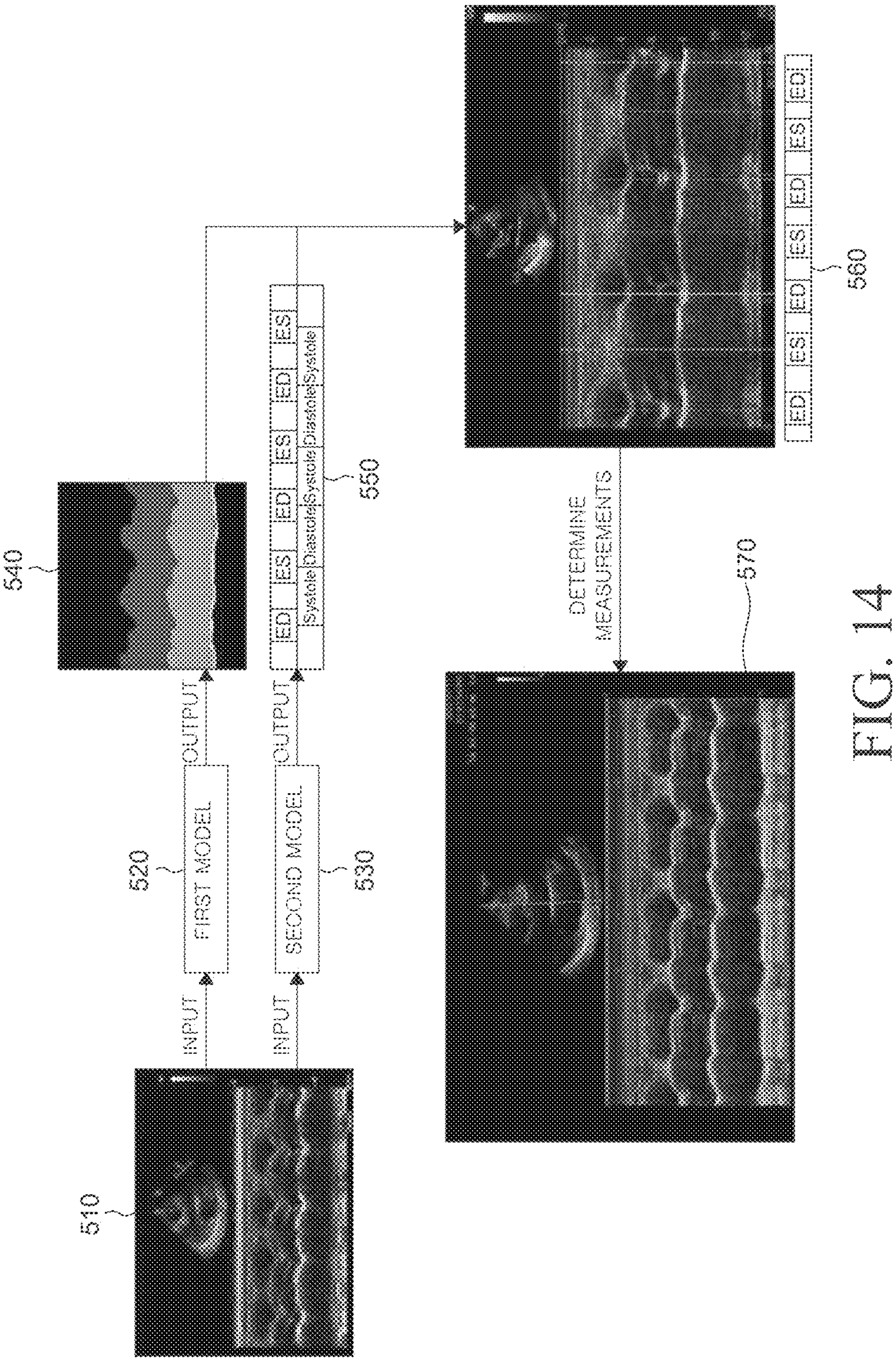
FIGS. 14 to 19D are exemplary diagrams of a method for providing information on an M-mode ultrasound image according to an embodiment of the present invention.

More specifically, referring to FIG. 14 together, the information provision server 300 for the M-mode ultrasound image may output a plurality of cardiac tomographic regions 540 when an M-mode ultrasound image 510 is input to a first model 520 at step (S420) where the plurality of cardiac tomographic regions are segmented. A detailed description of the first model will be described below in FIG. 15.

Figure 16A:
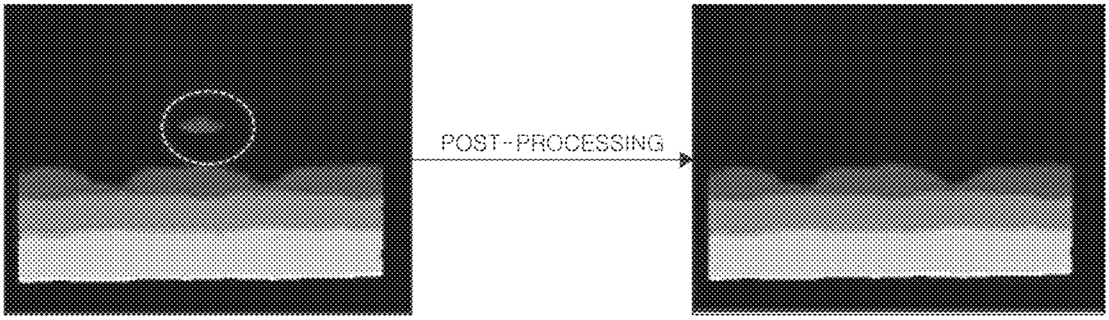
Figure 16B:
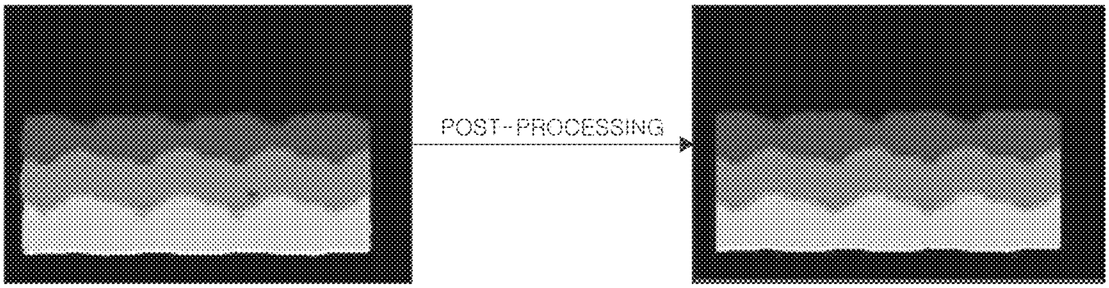

Meanwhile, referring to FIGS. 16A and 16B, the information provision server 300 for the M-mode ultrasound image may perform post-processing on the plurality of segmented cardiac tomographic regions. At this time, referring to FIG. 16A, the information provision server 300 for the M-mode ultrasound image may remove the segmented regions other than the M-mode region. In addition, referring to FIG. 16B, holes in the M-mode segmented regions may be filled. Here, the method of performing the post-processing is not limited to the above-mentioned method, and may be performed in various post-processing methods.

Referring back to FIG. 13, the information provision server 300 for the M-mode ultrasound image predicts diastole and systole in the M-mode ultrasound image (S430). At this time, the information provision server 300 for the M-mode ultrasound image may use a second model trained to predict diastole and systole in the M-mode ultrasound image by inputting the M-mode ultrasound image. Here, the second model may be a model that predicts end-diastole and end-systole of the M-mode ultrasound image. As another example, the second model may be a model that predicts each period of diastole and systole of the M-mode ultrasound image.

Figure 17A:
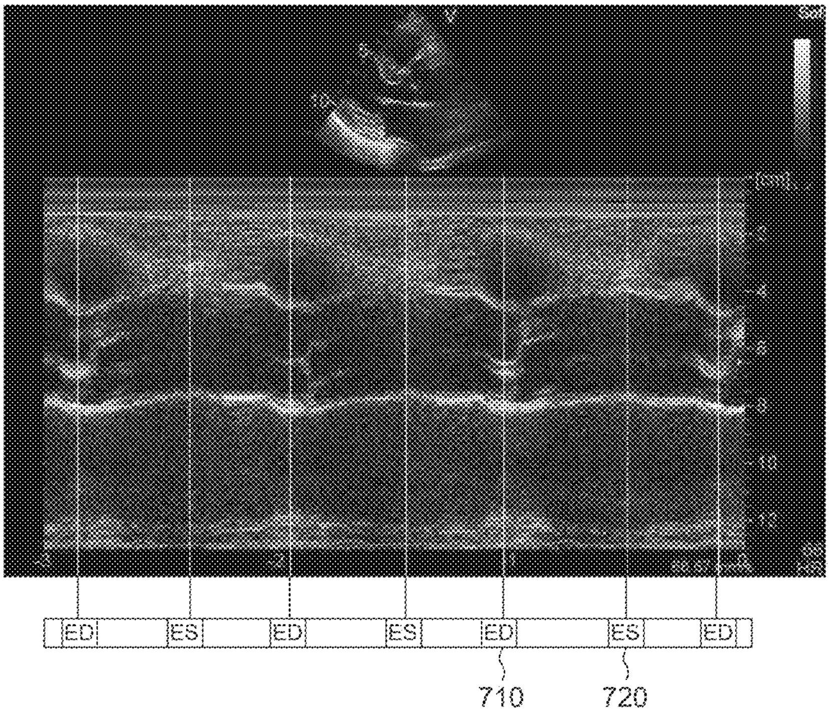
Figure 17B:
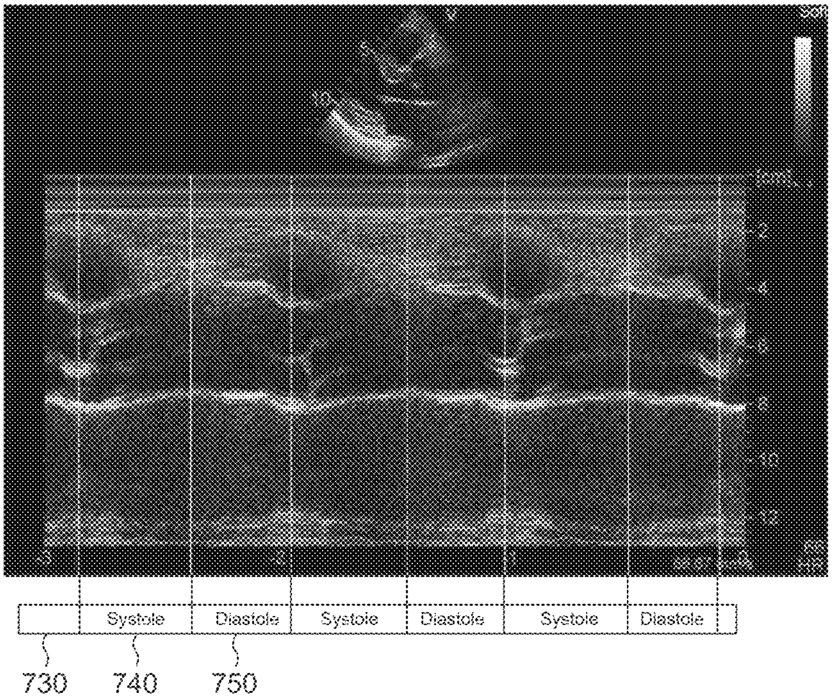

More specifically, referring to FIGS. 17A and 17B, the information provision server 300 for the M-mode ultrasound image may predict diastole and systole in the M-mode ultrasound image. At this time, referring to FIG. 17A, the information provision server 300 for the M-mode ultrasound image may predict and determine end-diastole 710 and end-systole 720 in the M-mode ultrasound image. As another example, referring to FIG. 17B, the information provision server 300 for the M-mode ultrasound image may predict and determine a systolic period 740 and a diastolic period 750. At this time, the information provision server 300 for the M-mode ultrasound image may not reflect a region 730 where a portion of the systole or diastole is received to the training of the second model.

Referring to FIG. 14, the information provision server 300 for the M-mode ultrasound image may output predicted diastole and systole 550 when an M-mode ultrasound image 510 is input into a second model 530 in step (S420) of predicting the diastole and systole in the M-mode ultrasound image. The method according to FIG. 14 includes determinations of ED and ES periods 560 and measurements 570 that may be correlative to the periods 434 and the measurements 442 of FIG. 4, respectively.

Figure 15:
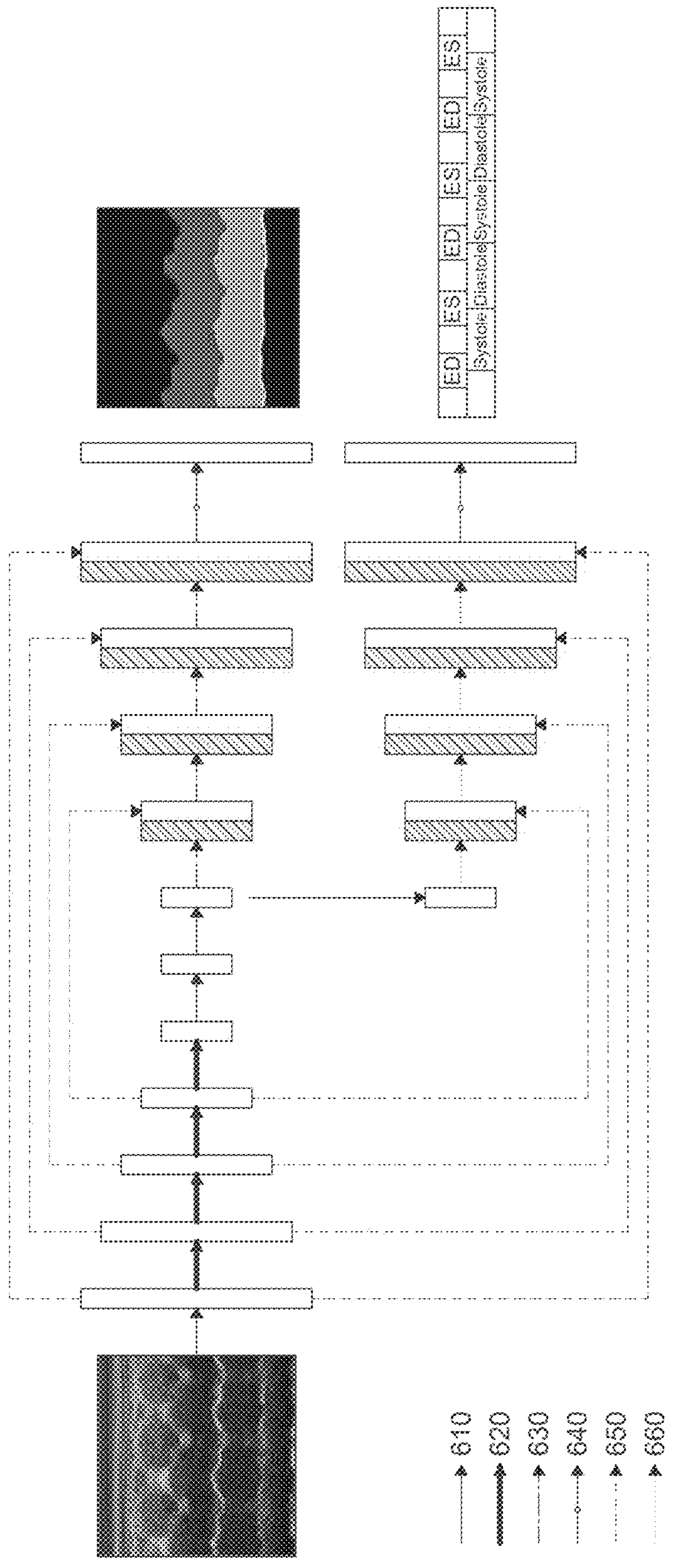

More specifically, referring to FIG. 15, the first model and the second model may be configured by a sampling stage and an upsampling stage. At this time, the first model and the second model may share the sampling stage. Here, the first model and the second model may be configured in a multi-task learning manner. For example, the first model and the second model may be configured with a U-Net structure.

For example, the sampling stage may consist of processes of tool 1 610 and tool 2 620. At this time, the tool 1 610 may be configured by a process of 3×3 Convolution-Batch Normalization-Rectified Linear Unit. Here, the 3×3 Convolution consists of a 3×3 sized filter, the Batch Normalization prevents input values from being biased by re-aligning the mean and standard deviation of the input values, and Rectified Linear Unit may remove values below the reference value. Meanwhile, the tool 2 620 may be configured by performing 3×3 Convolution-Batch Normalization-Rectified Linear Unit twice and a 2×2 Max Pool process. At this time, the 2×2 Max Pool may extract the largest value in a 2×2 sized filter area.

Meanwhile, in the upsampling stage, the first and second models may be differently configured. At this time, the filter size of the upsampling stage of the second model, i.e., the size of Convolution, may be smaller than the filter size of the upsampling stage of the first model. Here, the upsampling stage of the first model may consist of tool 3 630, tool 4 640, and tool 5 650. At this time, the tool 3 630 may be configured by a process of performing Upsampling, Concatenate and 3×3 Convolution-Batch Normalization-Rectified Linear Unit twice. Here, the tool 4 640 may be configured by 3×3 Convolution. In addition, the tool 5 650 may be configured by Concatenate. Meanwhile, the upsampling stage of the second model may consist of tool 4 640, tool 5 650, and tool 6 660. At this time, the tool 5 650 is identical to the upsampling stage of the first model, but the tool 4 640 may be configured by 1×1 convolution. Here, the tool 6 660 may be configured by a process of performing Upsampling, Concatenate, and 1×1 Convolution-Batch Normalization-Rectified Linear Unit twice. However, the first model and the second model are not limited to the above-mentioned U-Net structure, and the first model may be configured by any one of models that input the M-mode ultrasound image and output the plurality of cardiac tomographic regions, and the second model may be configured by any one of models that input the M-mode ultrasound image and output predictions of diastole and systole in the M-mode ultrasound image.

Referring back to FIG. 13, the information provision server 300 for the M-mode ultrasound image provides measurements of the plurality of segmented cardiac tomographic regions to the medical staff device 100 (S440). At this time, the information provision server 300 for the M-mode ultrasound image may determine measurements for the plurality of segmented cardiac tomographic regions based on the diastole and the systole predicted from the second model. Here, the information provision server 300 for the M-mode ultrasound image may determine measurements for the plurality of cardiac tomographic regions based on the end-diastole and the end-systole provided from the second model. As another example, the information provision server 300 for the M-mode ultrasound image may determine measurements for the plurality of cardiac tomographic regions at transition points of each period of the diastole and systole based on each period of the diastole and systole provided from the second model.

Hereinafter, evaluation results for measurements according to information providing methods according to various embodiments of the present invention will be described with reference to FIGS. 18A to 18E.

Figure 18A:
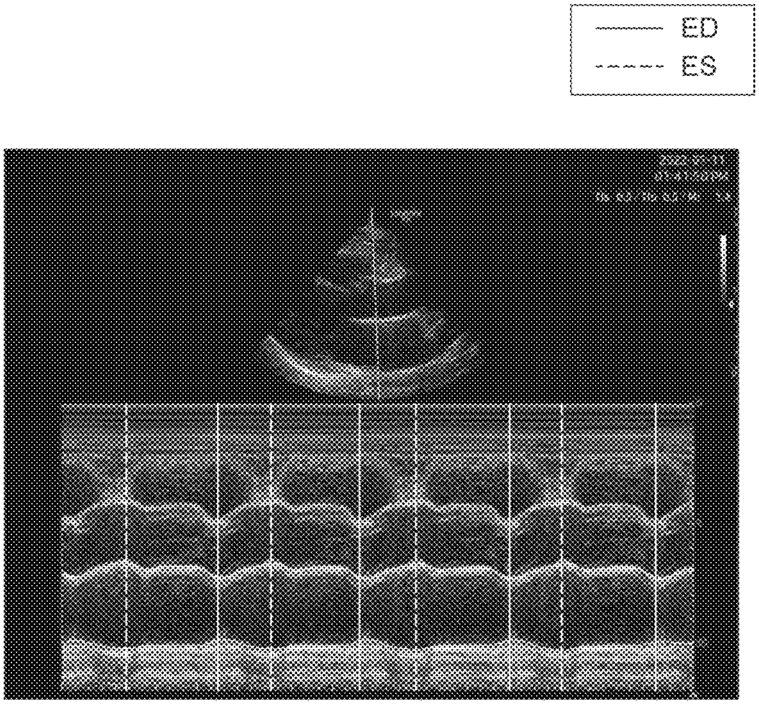
Figure 18B:
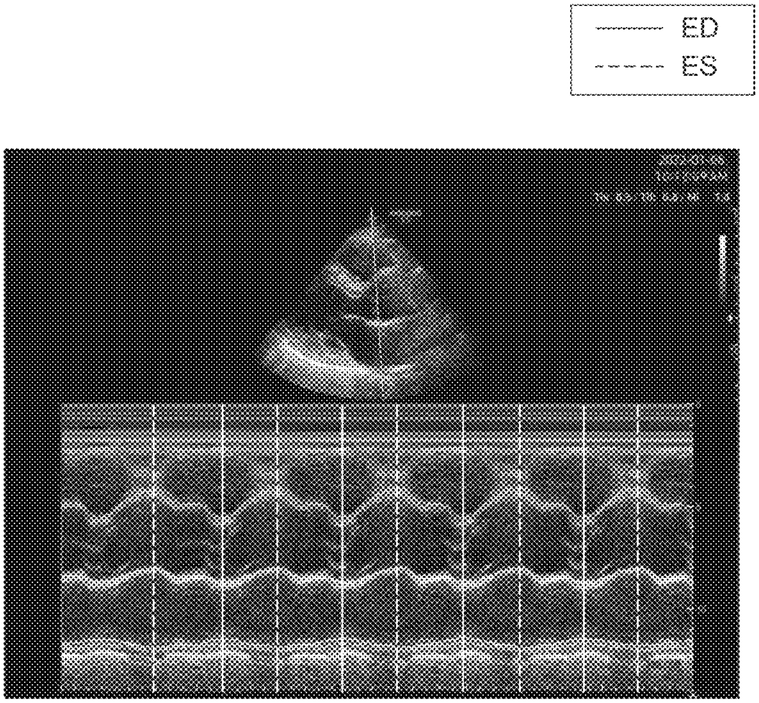

First, FIGS. 18A and 18B may be correlated with the results of Sinus Rhythm of a normal patient. At this time, the Sinus Rhythm may be any heart rhythm made when depolarization of the myocardium starts in the sinoatrial node. It may be seen that a second embodiment according to a method for providing information on an M-mode ultrasound image according to an embodiment of the present invention accurately predicts end-diastole (ED) and end-systole (ES) for a normal patient.

Figure 18C:
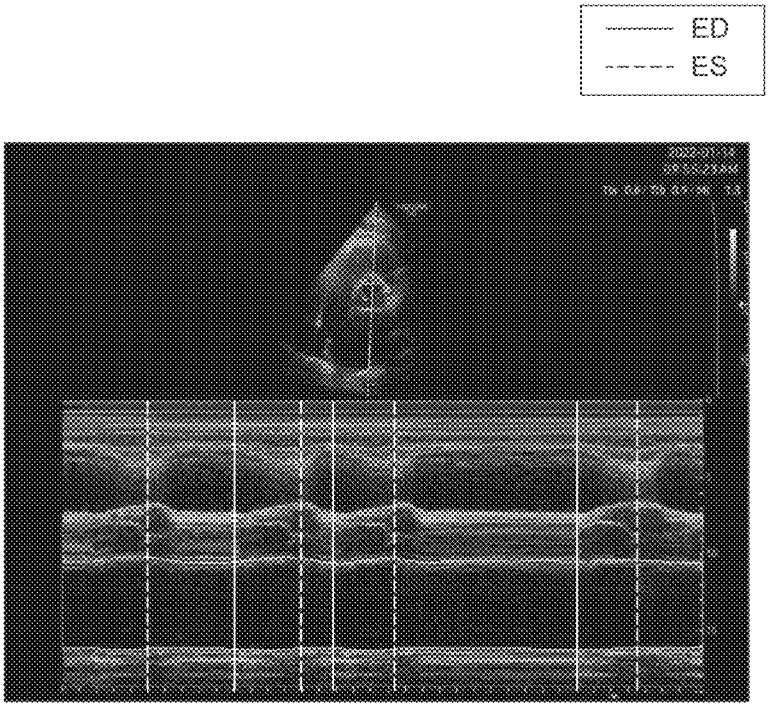
Figure 18D:
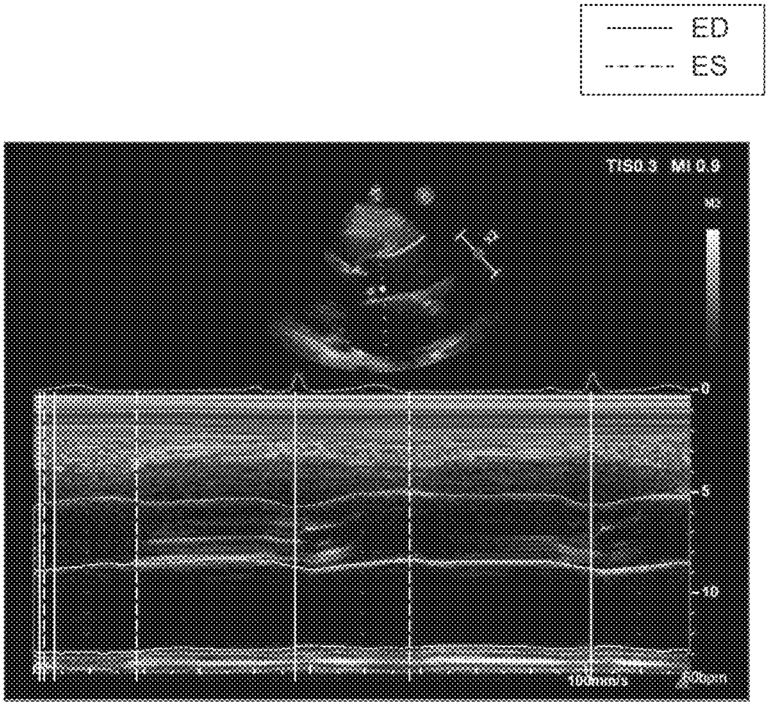
Figure 18E:
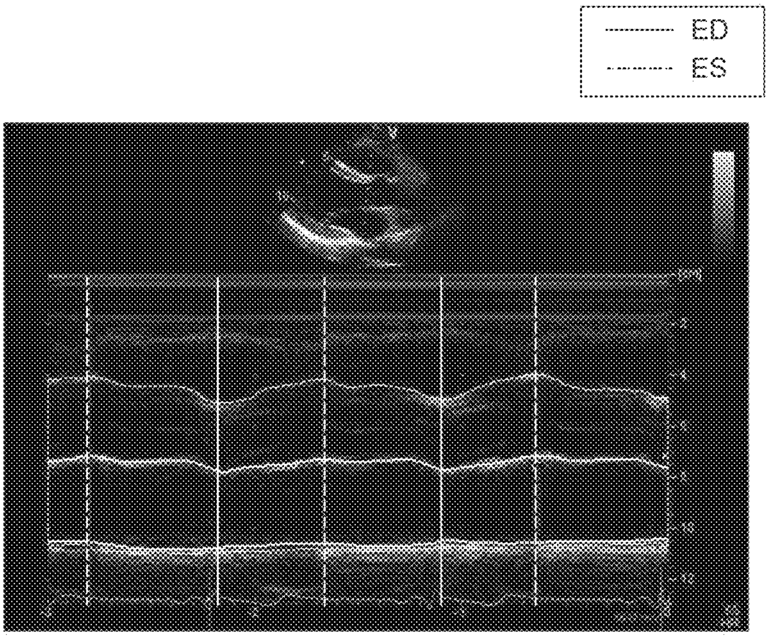

Here, FIGS. 18C to 18E may relate to the results of patients with Atrial Fibrillation. At this time, the Atrial Fibrillation is a condition in which the contraction of the atrium is lost and contracts irregularly, which may be a type of arrhythmia. Here, referring to FIG. 18 together, it may be confirmed that the second embodiment of the method for providing information on the M-mode ultrasound image according to one embodiment of the present invention accurately predicts end-diastole (ED) and end-systole (ES), even in an irregular pattern in which a distance between the predicted end-diastole (ED) and end-systole (ES) of FIGS. 18C to 18E, which are diagrams of a patient with Atrial Fibrillation, is longer than a distance between the predicted end-diastole (ED) and end-systole (ES) of FIGS. 18A and 18B, which are diagrams of a normal patient.

Hereinafter, a segmentation model and measurements used in various embodiments of the present invention will be described with reference to FIGS. 19A to 19D.

Figure 19A:
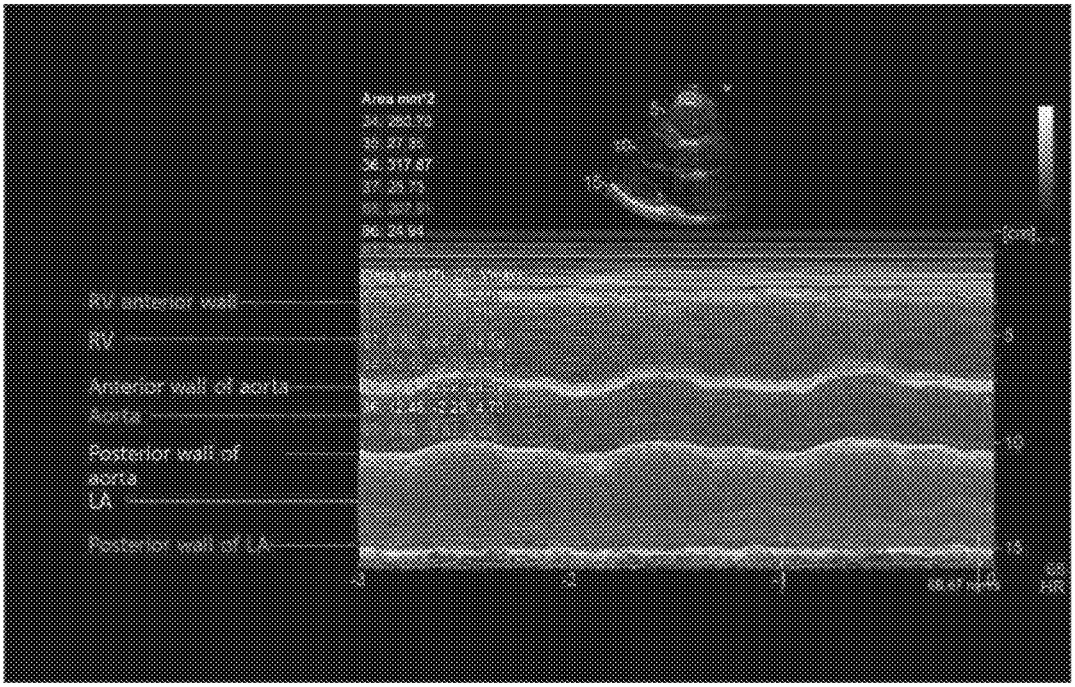
Figure 19B:
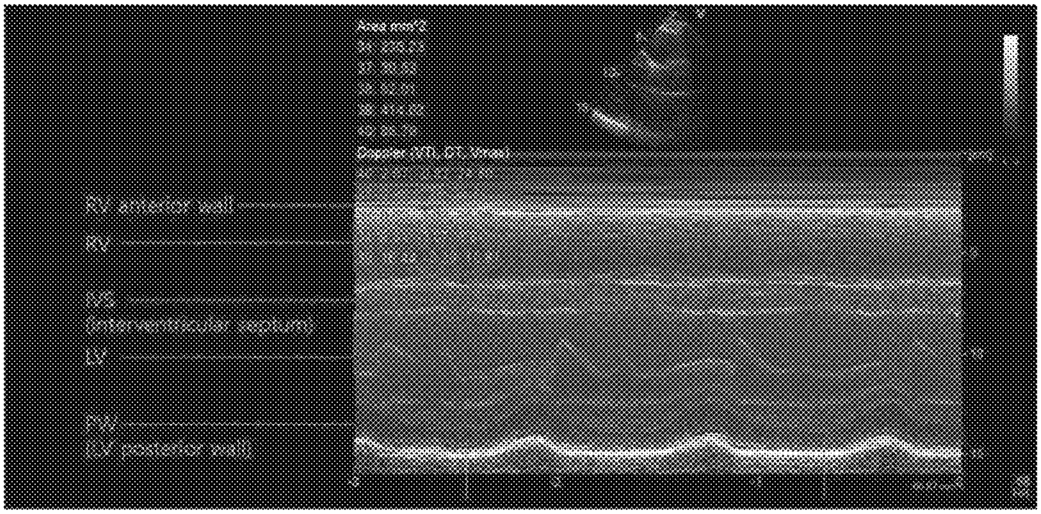
Figure 19C:
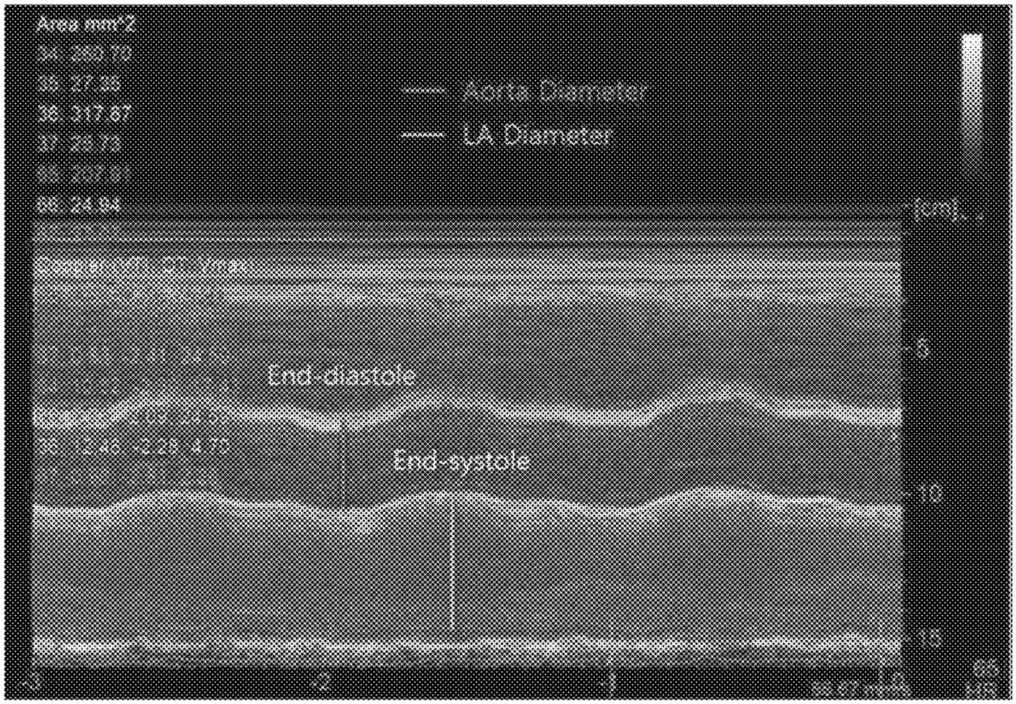
Figure 19D:
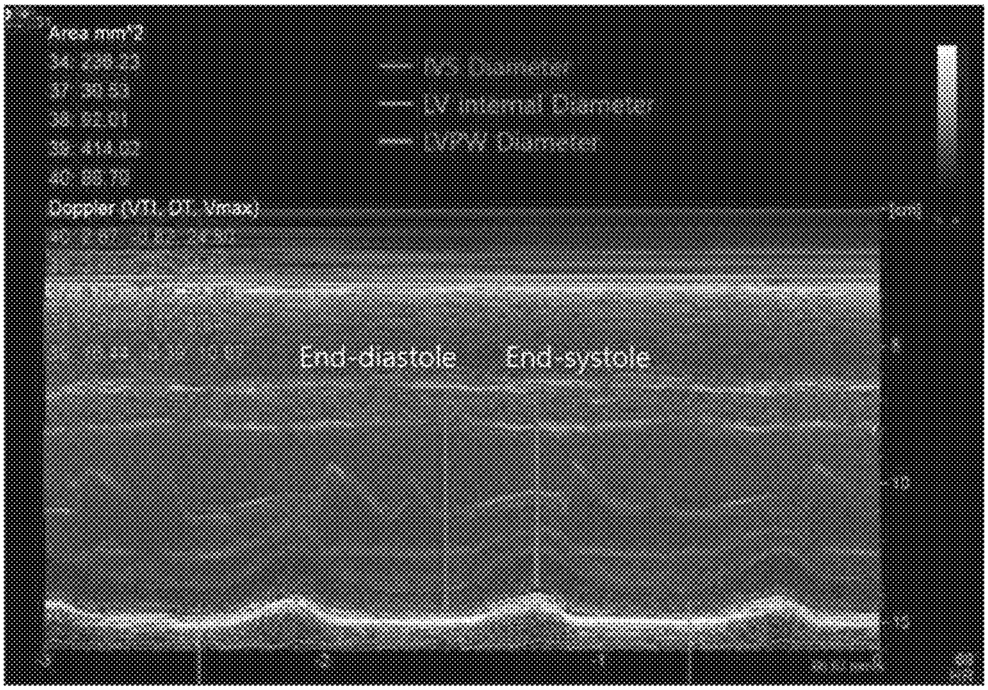

FIGS. 19A and 19B exemplarily illustrate training data of a segmentation model used in various embodiments of the present invention, and FIGS. 19C and 19D exemplarily illustrate measurements determined in a method for providing information on an M-mode ultrasound image according to various embodiments of the present invention.

First, referring to FIG. 19A, a segmentation model may use an M-mode ultrasound image for training, which is labeled with seven regions of the RV anterior wall, the right ventricle, the anterior wall of aorta, the aorta, the posterior wall of aorta, the left atrium, and the posterior wall of LA. That is, the segmentation model may be a model trained to segment the regions for left atrium-aorta (LA-Ao) analysis.

Next, referring to FIG. 19B, the segmentation model may use an M-mode ultrasound image for training, which is labeled with five regions of the RV anterior wall, the right ventricle, the interventricular septum, the left ventricle, and the LV posterior wall. That is, the segmentation model may be a model trained to segment the regions for left ventricle (LV) analysis. Meanwhile, the M-mode images for training are not limited thereto, and the labeling regions may vary depending on a region to be segmented and a analysis goal.

Next, referring to FIG. 19C, the measurements may be an LA diameter corresponding to systole and an aorta diameter corresponding to end-diastole.

Referring to FIG. 19D, the measurements may be an interventricular septum (IVS) diameter, an LV internal diameter (LV 71-37 2022 Apr. 22 internal diameter; LVID), and an LV posterior wall (LVPW) diameter corresponding to each of end-systole and end-diastole.

However, the measurements are not limited to those described above and may be set more diversely depending on an analysis goal.

Although the exemplary embodiments of the present invention have been described in detail with reference to the accompanying drawings, the present invention is not limited thereto and may be embodied in many different forms without departing from the technical concept of the present invention. Therefore, the exemplary embodiments of the present invention are provided for illustrative purposes only but not intended to limit the technical concept of the present invention. The scope of the technical concept of the present invention is not limited thereto. Therefore, it should be appreciated that the aforementioned embodiments are illustrative in all aspects and are not restricted. The protective scope of the present invention should be construed on the basis of the appended claims, and all the technical ideas in the equivalent scope thereof should be construed as falling within the scope of the present invention.

What is claimed is:

1. A method implemented by a processor, the method comprising:

receiving an M-mode ultrasound image of a subject;

segmenting a plurality of cardiac tomographic regions within the M-mode ultrasound image, respectively, by using a first model that is trained so as to segment the M-mode ultrasound image into the plurality of cardiac tomographic regions by inputting the M-mode ultrasound image;

obtaining a plurality of post-processed cardiac tomographic regions by post-processing the plurality of segmented cardiac tomographic regions, the post-processing including at least one of removing segmented regions outside an M-mode region of the M-mode ultrasound image, or filling holes within the plurality of segmented cardiac tomographic regions;

determining diastole and systole within the M-mode ultrasound image, by using a second model that is trained to predict the diastole and the systole of the M-mode ultrasound image by inputting the M-mode ultrasound image; and determining measurements for the plurality of segmented post-processed cardiac tomographic regions based on the diastole and the systole, wherein each of the first model and the second model includes a sampling stage and an upsampling stage, the first model and the second model sharing one sampling stage, and wherein the upsampling stage of the second model has a filter size smaller than a filter size of the upsampling stage of the first model.

2. The method of claim 1, wherein the second model is a model that predicts end-diastole and end-systole by inputting the M-mode ultrasound image.

3. The method of claim 2, wherein the determining of the measurements includes determining measurements for the plurality of cardiac tomographic regions based on the predicted end-diastole and the end-systole.

4. The method of claim 1, wherein the second model is a model that predicts each period of the diastole and the systole by inputting the M-mode ultrasound image.

5. The method of claim 4, wherein the determining of the measurements includes determining measurements for the plurality of cardiac tomographic regions at transition points of each predicted period of the diastole and the systole.

6. The method of claim 1, wherein the plurality of cardiac tomographic regions are at least two regions selected from the RV anterior wall, the right ventricle (RV), the aorta, the anterior wall of the aorta, the posterior wall of the aorta, the left atrium (LA), and the posterior wall of the LA, and the measurements are an aorta diameter or a LA diameter.

7. The method of claim 1, wherein the plurality of cardiac tomographic regions are at least two regions selected from the right ventricle (RV), the RV anterior wall, the interventricular septum (IVS), the left ventricle (LV), and the LV posterior wall, and the measurements are at least one of an IVS diameter, an LV internal diameter (LVID), and an LV posterior wall diameter.

8. A device comprising:

a receiver configured to receive an M-mode ultrasound image of a subject; and a processor operably connected with the receiver and configured to segment a plurality of cardiac tomographic regions within the M-mode ultrasound image, respectively, by using a first model that is trained so as to segment the M-mode ultrasound image into the plurality of cardiac tomographic regions by inputting the M-mode ultrasound image, determine diastole and systole within the M-mode ultrasound image, by using a second model that is trained to predict the diastole and the systole of the M-mode ultrasound image by inputting the M-mode ultrasound image, and determine measurements for the plurality of segmented cardiac tomographic regions based on the diastole and the systole, wherein each of the first model and the second model includes a sampling stage and an upsampling stage, the first model and the second model sharing one sampling stage, and wherein the upsampling stage of the second model has a filter size smaller than a filter size of the upsampling stage of the first model.

9. The device of claim 8, wherein the second model is a model that predicts end-diastole and end-systole by inputting the M-mode ultrasound image.

10. The device of claim 9, wherein the determining of the measurements includes determining measurements for the plurality of cardiac tomographic regions based on the predicted end-diastole and the end-systole.

11. The device of claim 8, wherein the second model is a model that predicts each period of the diastole and the systole by inputting the M-mode ultrasound image.

12. The device of claim 11, wherein the determining of the measurements includes determining measurements for the plurality of cardiac tomographic regions at transition points of each predicted period of the diastole and the systole.

* * * * *